(12) United States Patent
Robinson et al.

(10) Patent No.: US 10,636,612 B2
(45) Date of Patent: Apr. 28, 2020

(54) MAGNETIC ASSIST ASSEMBLY HAVING HEAT DISSIPATION

(71) Applicant: Varex Imaging Corporation, Salt Lake City, UT (US)

(72) Inventors: Vance Scott Robinson, South Jordan, UT (US); Kasey Otho Greenland, West Jordan, UT (US); Neil Bostrom, Millcreek, UT (US)

(73) Assignee: Varex Imaging Corporation, Salt Lake City, UT (US)

( * ) Notice: Subject to any disclaimer, the term of this patent is extended or adjusted under 35 U.S.C. 154(b) by 29 days.

(21) Appl. No.: 16/146,914

(22) Filed: Sep. 28, 2018

(65) Prior Publication Data

US 2020/0105495 A1  Apr. 2, 2020

(51) Int. Cl.
*H01J 35/10* (2006.01)
*A61B 6/03* (2006.01)

(52) U.S. Cl.
CPC ............ *H01J 35/106* (2013.01); *A61B 6/032* (2013.01); *H01J 35/103* (2013.01); *H01J 2235/1013* (2013.01); *H01J 2235/1026* (2013.01); *H01J 2235/1073* (2013.01); *H01J 2235/1295* (2013.01)

(58) Field of Classification Search
CPC ...... A61B 6/032; H01J 35/103; H01J 35/106; H01J 2235/1013; H01J 2235/1026; H01J 2235/1073; H01J 2235/1295
See application file for complete search history.

(56) References Cited

U.S. PATENT DOCUMENTS

| | | | | |
|---|---|---|---|---|
| 4,504,965 A | | 3/1985 | Ebersberger | |
| 4,583,794 A | * | 4/1986 | Takahara | F16C 32/0465 310/90.5 |
| 5,710,469 A | * | 1/1998 | Ries | F16C 32/0438 310/90.5 |
| 5,737,387 A | * | 4/1998 | Smither | H01J 35/106 378/130 |
| 6,055,294 A | * | 4/2000 | Foerst | H01J 35/30 378/137 |
| 6,091,799 A | * | 7/2000 | Schmidt | H01J 35/30 378/113 |
| 6,118,203 A | * | 9/2000 | Hansen | H01J 35/101 310/179 |
| 6,128,367 A | * | 10/2000 | Foerst | H01J 35/30 378/121 |
| 6,198,803 B1 | | 3/2001 | Osama et al. | |
| 6,327,340 B1 | | 12/2001 | Runnoe | |
| 6,762,522 B2 | | 7/2004 | Steinmeyer | |
| 7,203,280 B2 | | 4/2007 | Ann et al. | |
| 7,206,380 B2 | | 4/2007 | Ann et al. | |

(Continued)

*Primary Examiner* — Mark R Gaworecki
(74) *Attorney, Agent, or Firm* — Maschoff Brennan

(57) ABSTRACT

In one example, a lift assembly may exert a force on a rotatable anode of an X-ray tube. The lift assembly may include a lift shaft and a lift electromagnet. The lift shaft may be coupled to the anode and may be configured to rotate around an axis of rotation of the anode. The lift electromagnet may be configured to apply a magnetic force to the lift shaft in a radial direction. The lift electromagnet may include a first pole and a second pole oriented towards the lift shaft. Windings may be positioned around the first pole. The lift assembly may include a heat dissipating structure.

20 Claims, 20 Drawing Sheets

(56) References Cited

U.S. PATENT DOCUMENTS

| | | |
|---|---|---|
| 8,385,505 B2 | 2/2013 | Coon et al. |
| 2004/0021382 A1* | 2/2004 | Steinmeyer ......... F16C 32/0438 |
| | | 310/90.5 |
| 2004/0080727 A1 | 4/2004 | Emoto |
| 2010/0027753 A1* | 2/2010 | Venugpal .............. H01J 35/101 |
| | | 378/130 |
| 2010/0322383 A1* | 12/2010 | Coon .................... H01J 35/103 |
| | | 378/127 |
| 2012/0257722 A1* | 10/2012 | Heidrich .............. H01J 35/305 |
| | | 378/131 |
| 2015/0117604 A1 | 4/2015 | Chrost |
| 2016/0310086 A1* | 10/2016 | Besson ................ A61B 6/4007 |
| 2017/0301504 A1 | 10/2017 | Burke et al. |
| 2018/0366237 A1* | 12/2018 | Rogers ................... H01J 35/06 |

* cited by examiner

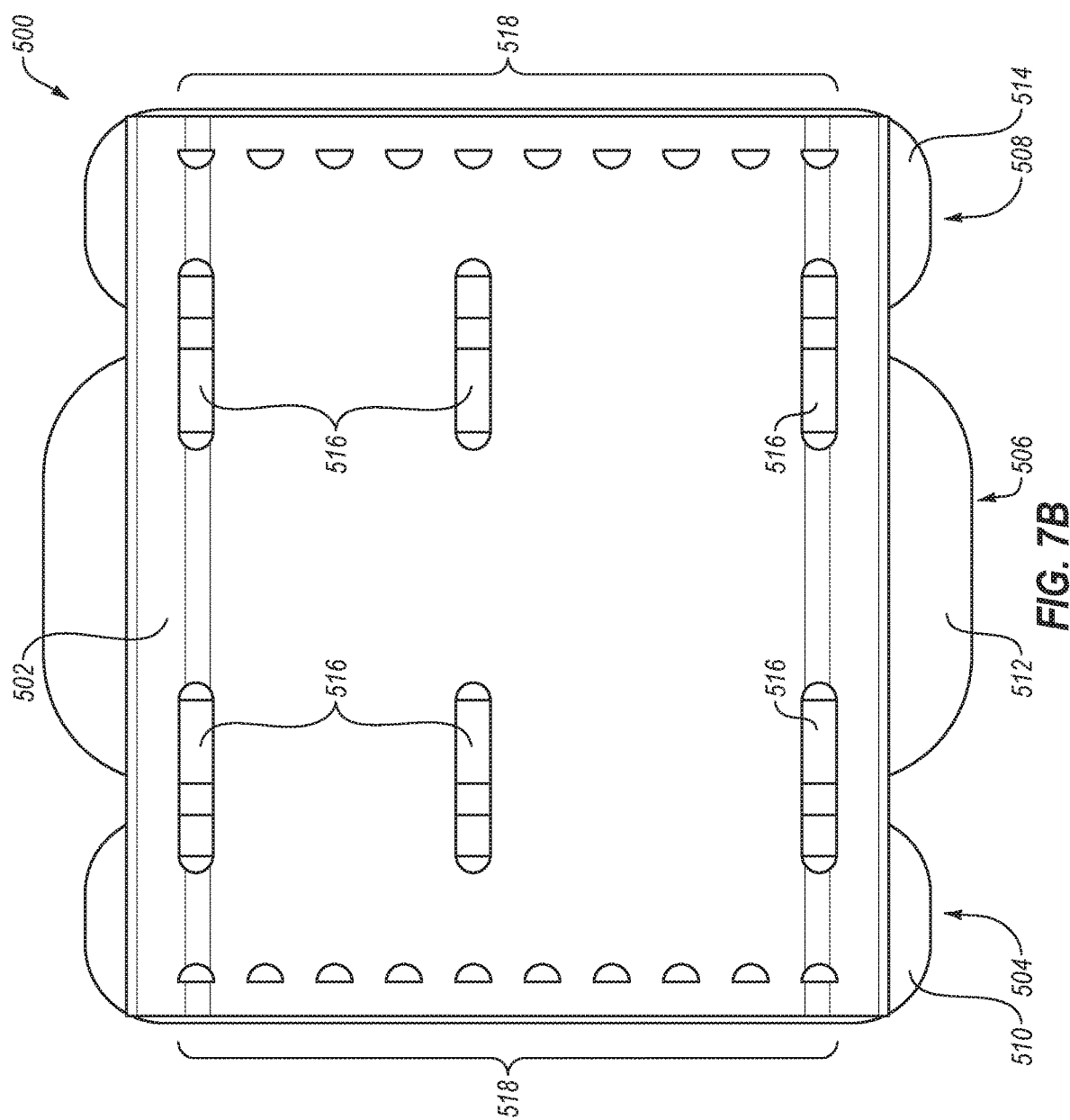

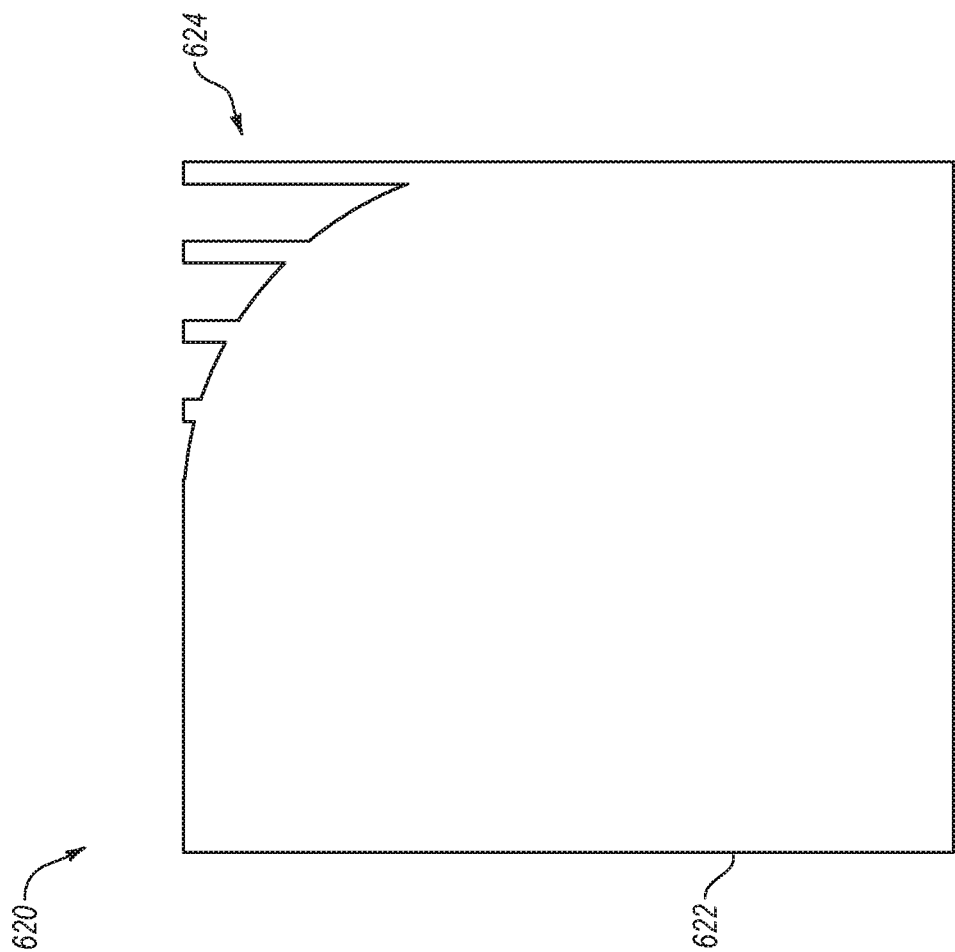

MAGNETIC ASSIST ASSEMBLY HAVING HEAT DISSIPATION

BACKGROUND

The present disclosure generally relates to X-ray imaging systems, including embodiments relating to magnetic lift assemblies for X-ray sources used in X-ray imaging systems.

X-ray imaging systems typically include an X-ray source, a detector, and a support structure, such as a gantry, for the X-ray source and the detector. In operation, the X-ray source typically emits radiation, such as X-rays, toward an object. The radiation passes through the object and impinges on the detector. The detector receives the radiation and transmits data representative of the received radiation.

The X-ray source includes a cathode and an anode separated by a vacuum gap. X-rays are produced by applying an electrical current to an emitter of the cathode which emits electrons. The electrons accelerate towards and then impinge upon the anode. When the electrons impinge on the anode, some of the energy is converted to X-rays. The majority of the energy in the incident electron beam converts to heat in the anode. Because of high temperatures generated when the electron beam strikes the target, the anode can include features to distribute the heat generated, such as rotating a disc-shaped anode target. The disc-shaped anode target may be rotated by an induction motor via a bearing assembly.

The X-ray source and radiation detector can be components in an X-ray imaging system, such as a computed tomography (CT) system or scanner, which includes a gantry that rotates both the X-ray source and the detector to generate various images of the object at different angles. The gravitational (G) forces imposed by the rotation of the gantry and/or the rotation of the anode may result in stresses on components of the X-ray source. In particular, G forces resulting from the rotation of the gantry and/or the anode may result in stress on the bearing assembly of X-ray sources with rotating anodes. In addition, the stress on the bearing assembly may increase as rotation speeds increase, but increased rotation speeds may be desirable for high-performance X-ray sources and CT systems. The present disclosure includes solutions related to reducing the stresses on bearing assemblies in rotating X-ray imaging systems (e.g., CT scanners).

The subject matter claimed herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE DRAWINGS

FIG. 7B illustrates a top view of the lift electromagnet of FIG. 7A.

FIG. 9 is a schematic cross section of another example of a lift electromagnet.

DETAILED DESCRIPTION

Reference will be made to the drawings and specific language will be used to describe various aspects of the disclosure. Using the drawings and description in this manner should not be construed as limiting its scope. Additional aspects may be apparent in light of the disclosure, including the claims, or may be learned by practice.

The invention relates to embodiments for dissipating heat generated by lift assemblies which may be used to reduce loads on rotating components of an X-ray tube. X-ray tubes generate heat during operation. Accordingly, X-ray tubes may include features such as rotating anodes to spread the heat generated. However, rotating components of a rotating anode may experience forces resulting from gantry rotation in CT systems. Thus, lift assemblies may be incorporated into X-ray tubes to counter balance the forces on rotating components. Such lift assemblies may also generate heat that may need to be dissipated. Accordingly, disclosed embodiments include example configurations to dissipate heat generated by the lift electromagnet.

Reference will now be made to the drawings to describe various aspects of example embodiments of the disclosure. It is to be understood that the drawings are diagrammatic and schematic representations of such example embodiments, and are not limiting of the disclosure, nor are they necessarily drawn to scale.

Figure 1:
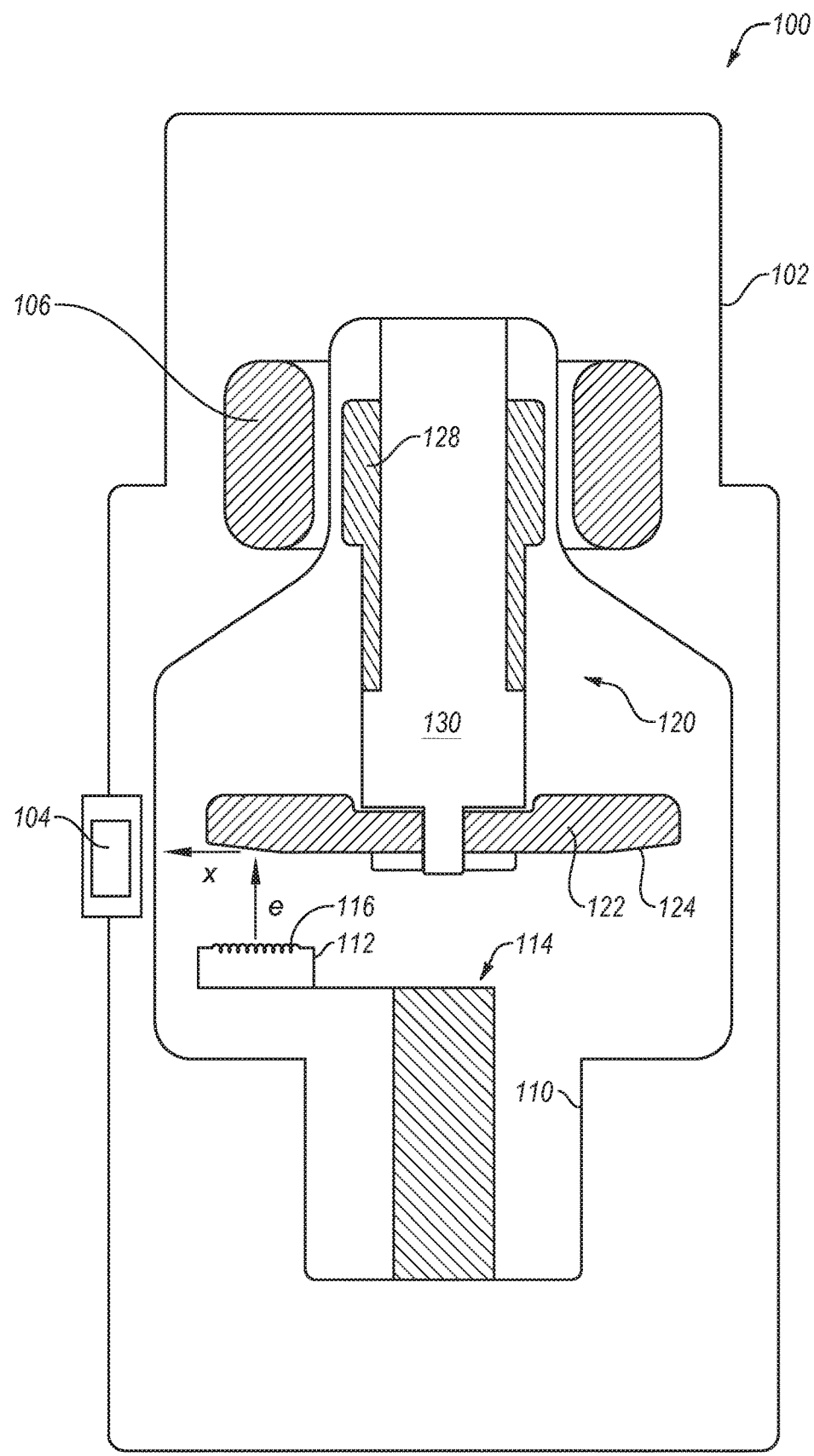
FIG. 1 illustrates a schematic diagram of an example X-ray source.

FIG. 1 is a schematic diagram of an example rotary or rotating anode X-ray source 100 with a rotatable disc-shaped anode 122. The X-ray source 100 includes a housing 102 and an X-ray insert 110 within the housing 102. The housing 102 encloses the insert 110. A fluid coolant such as a dielectric oil or air may fill the space or cavity between the housing 102 and the insert 110 to dissipate heat generated by the X-ray source 100.

A cathode assembly 114 including a cathode 112 and an anode assembly 120 are positioned within an evacuated enclosure (or vacuum envelope) defined by the insert 110. The anode assembly 120 includes the anode 122, a bearing assembly 130, and a rotor 128 mechanically coupled to the bearing assembly 130. The anode 122 is spaced apart from and oppositely disposed to the cathode 112. The anode 122 and cathode 112 are connected in an electrical circuit that allows for the application of a high voltage difference (or high electric potential) between the anode 122 and the cathode 112. The cathode 112 includes an electron emitter 116 that is connected to a power source.

Prior to operation of the X-ray source 100, the insert 110 may be evacuated to create a vacuum, which may be enclosed by the insert 110. During operation, heat and electrical potential is applied to the electron emitter 116 of the cathode 112 to cause electrons, denoted as "e" in FIG. 1, to be emitted from the cathode 112 by thermionic emission. The application of a high voltage differential between the anode 122 and the cathode 112 then causes the electrons "e" to accelerate from the electron emitter 116 toward a focal spot on a focal track 124 that is positioned on the anode 122. The focal track 124 may include, for example, a material having a high atomic ("high Z") number such as tungsten (W), rhenium (Re) or other suitable material. As the electrons "e" accelerate, they gain a substantial amount of kinetic energy, and upon striking the rotating focal track 124 some of this kinetic energy is converted into X-rays, denoted as "x" in FIG. 1.

The focal track 124 is oriented so that emitted X-rays "x" may travel through an X-ray source window 104. The window 104 includes an X-ray transmissive material, such as beryllium (Be), so the X-rays "x" emitted from the focal track 124 pass through the window 104 in order to strike an intended object and then a detector to produce an X-ray image.

As the electrons "e" strike the focal track 124, a significant amount of the kinetic energy of the electrons "e" results in heat, a large portion of which is transferred to the focal track 124, particularly in the region of the focal spot. To reduce the heat at a specific focal spot on the focal track 124, a disc-shaped anode target is rotated at high speeds, typically using an induction motor that includes a rotor 128 and a stator 106. The induction motor can be an alternating current (AC) electric motor in which the electric current in the rotor 128 needed to produce torque is obtained by electromagnetic coupling with the stator winding. The rotor 128 is mechanically coupled to the anode 122 through a hub of the bearing assembly 130 such that rotation of the rotor is transferred to the anode. In other configurations, the motor can be a direct current (DC) motor.

To avoid overheating the anode 122 from the heat generated by electrons "e", the rotor 128 rotates the anode 122 at a high rate of speed (e.g., 80-300 Hz) about a centerline of a shaft so that the region of the anode exposed to the beam of electrons "e" varies along the focal track 124. The X-ray source 100 can also include other cooling features to manage the heat generated by the anode 122 and the cathode 112.

An X-ray source (such as the X-ray source 100) and a radiation detector can be included in a rotational X-ray imaging system, such as a computed tomography (CT) scanner. CT involves the imaging of the internal structure of an object by collecting several projection images ("radiographic projections") in a single scan operation ("scan"), and is widely used in the medical field to view the internal structure of selected portions of the human body. Typically, several two-dimensional projections are made of the object, and a three-dimensional representation of the object is constructed from the projections using various tomographic reconstruction methods. From the three-dimensional image, conventional CT slices through the object can be generated. The two-dimensional projections are typically created by transmitting radiation from an X-ray source through the object and collecting the radiation onto a two-dimensional imaging device (i.e., radiation detector), or imager, which may include an array of pixel detectors (simply called "pixels"). One example of such a CT system is shown in FIG. 2A.

Figure 2A:
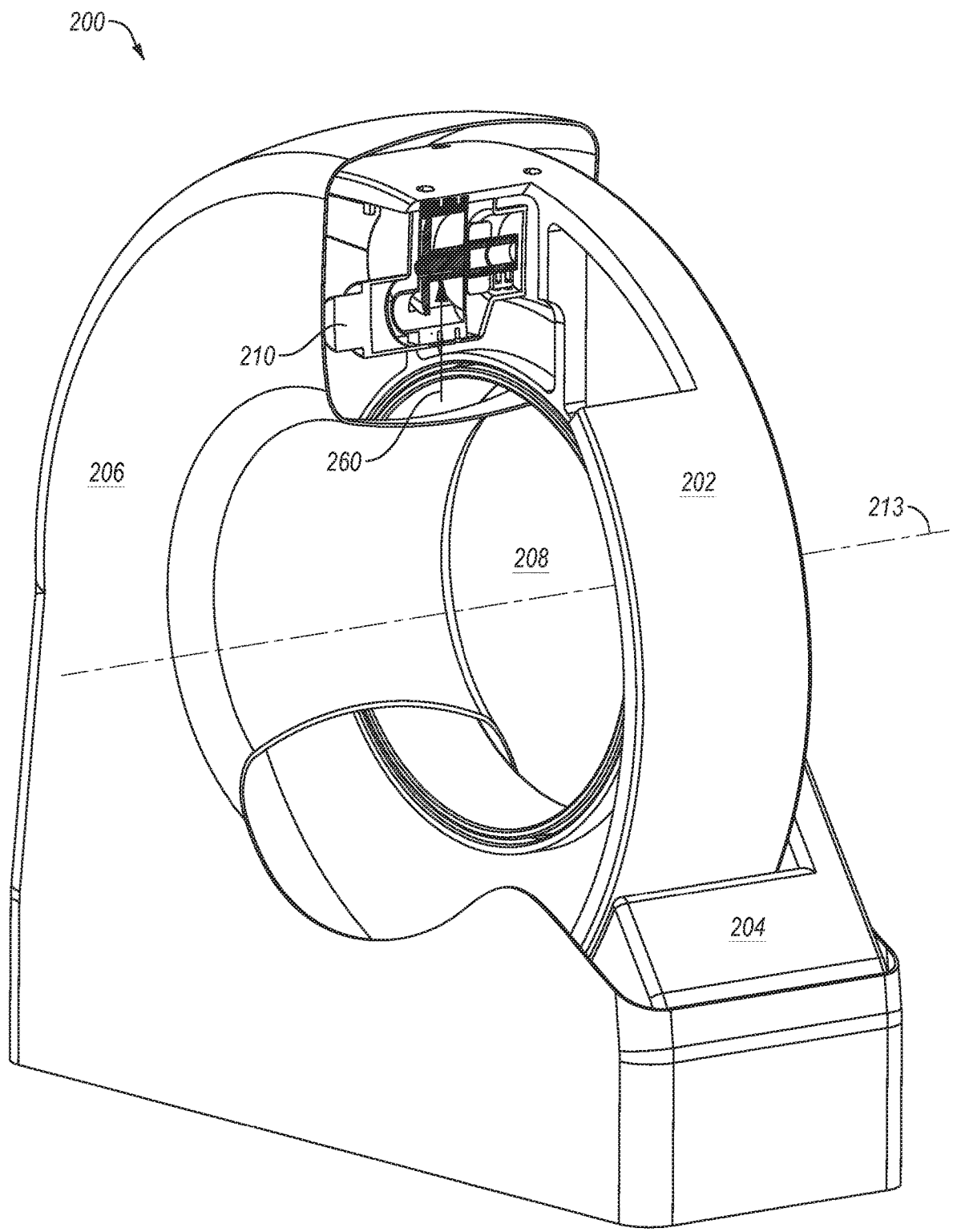
FIG. 2A illustrates a perspective view of an example gantry.

FIG. 2A illustrates an example of a gantry 200 of a rotating X-ray system. In some circumstances the gantry 200 may be referred to as a rotating assembly or a gantry assembly. The gantry 200 includes a stationary gantry frame 204 that supports a rotatable gantry frame 202. The rotatable gantry frame 202 may support an X-ray source 210 and a radiation detector or imager (not shown). The gantry 200 also includes a gantry cover 206 to enclose the rotating components and/or the stationary gantry frame 204 as well as provide an aesthetic covering.

The rotatable gantry frame 202 may include an annular shape (i.e., ring shape) that rotates about a center of axis in a gantry aperture 208 of the rotatable gantry frame 202. The centrifugal force (or gantry force), denoted via arrow 260, on components disposed on the rotatable gantry frame 202 may exceed a unit of gravitational force (g-force, G's, g's, or G loads), and may be a multiple of the g-force (e.g., 20 times the g-force). For example, components on the X-ray source 210, such as the bearing assembly, may experience a force of $37g$'s if the X-ray source 210 is mounted on the rotatable gantry frame 202 at a radius of 0.7 meters from the center of axis and the rotatable gantry frame 202 is rotating at 0.275 seconds/rotation (sec/rot).

Generally, it is desirable for CT scanners to operate at higher rotational gantry speeds. However, operating CT scanners with gantries that rotate at higher speeds may adversely affect X-ray source bearing life because the bearing assemblies experience larger forces (e.g., g-forces from gantry rotation). In such circumstances, higher gantry speeds, and resultant centrifugal forces 260, can decrease the life of the bearing assembly.

Some X-ray sources implement liquid metal bearings (LMB), which may be capable of effectively handling higher forces (e.g., g-forces). However, implementing LMB can significantly increase costs and may require significant changes to the system design (e.g., the design of the X-ray source).

Other X-ray sources may implement magnetic lift configurations to magnetically assist in supporting the rotating components of the X-ray source and to decrease the forces on the bearing assembly. In some circumstances, such configurations may be advantageous over LMB because they may be implemented in existing imaging systems and/or they may provide very cost effective backwardly compatible improvements. With attention to FIG. 2B, an example of a magnetic lift configuration will be described in further detail.

Figure 2B:
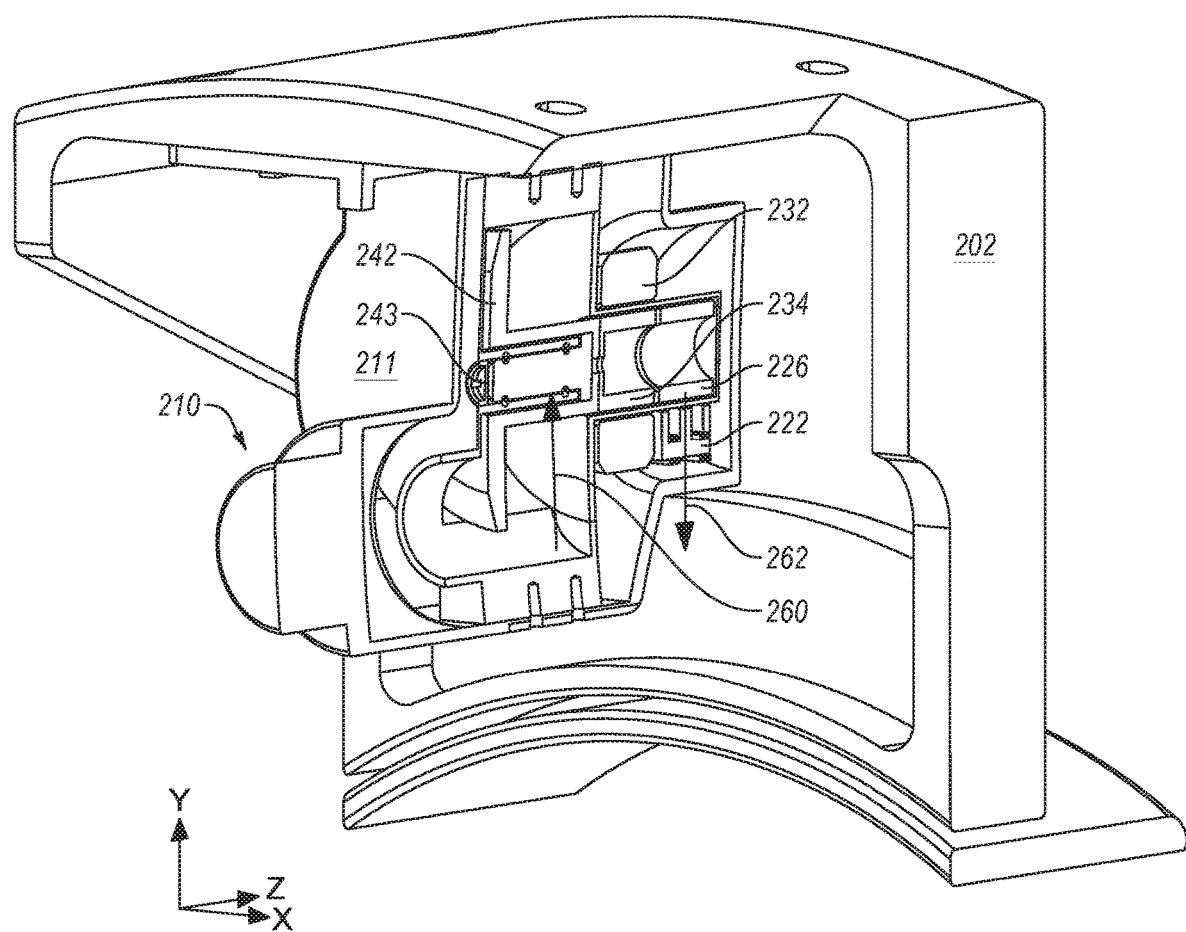
FIG. 2B illustrates a perspective view of a portion of the gantry of FIG. 2A that includes a rotating anode X-ray source.

FIG. 2B illustrates a portion of the gantry 200, and in particular, the X-ray source 210 attached to the rotatable gantry frame 202. The X-ray source 210 includes a source housing 211, an anode 242 that can receive electrons emitted by a cathode (112 of FIG. 1), a rotor 234 coupled to a shaft 243 of the anode 242, a stator 232 surrounding the rotor 234, a ferromagnetic lift shaft 226 coupled to the rotor 234, and a lift electromagnet 222 (or lift multipole electromagnet or electromagnet) that can provide a magnetic lift force, denoted via arrow 262, to the lift shaft 226 and thereby "lift" the rotor 234 and the shaft 243 of the anode 242 along the radial direction with respect to the axis of rotation of the gantry in opposition to the centrifugal force.

As used herein, lifting refers to an application of force along the radial direction of the lift shaft 226. The lifting or lift force can be an attractive force that pulls two components together (e.g., the lift shaft 226 and the lift electromagnet 222) or a repulsive or repelling force that pushes two components apart (e.g., the lift shaft 226 and the lift electromagnet 222). In this disclosure, reference will be made to the lifting or the lift force as an attractive force, but the lifting or the lift force can be a force with any magnitude (positive or negative) along the radial direction.

For descriptive purposes, FIG. 2B includes a Cartesian coordinate system with the y-axis in the vertical direction, the x-axis in the horizontal direction, and the z-axis orthogonal to the x-y plane. The rotation of the gantry 200 occurs in the x-y plane and the centerline of the shaft 243 of the anode 242 or the axis of rotation of the anode 242 extends parallel to the z-axis. During gantry rotation, a centrifugal force 260 is applied to the X-ray source 210 orthogonal-axis 213 of the gantry 200.

The lift electromagnet 222 may apply the magnetic lift force 262 (e.g., magnetic force, counter acting force, or balancing force) in substantially the opposite direction of the centrifugal force 260 so as to offset, dampen, reduce, or balance the forces (including the centrifugal force 260 of the gantry 200) on the bearing assembly or anode assembly. The magnetic lift force 262 may result in one or more of the following: reduce vibration or noise, increase bearing life, increase the bearing load capability, control thermal contact, improve the centering and precision of the rotating assembly, and allow the use of smaller bearings (e.g., ball bearings or other rotating bearings). Additionally or alternatively, the assistance of the magnetic lift force 262 may permit the use of other bearing types in a rotating anode X-ray source. In the case of medical imaging, reducing vibration and noise may also improve the patient's and/or medical staff's experience.

Figure 3A:
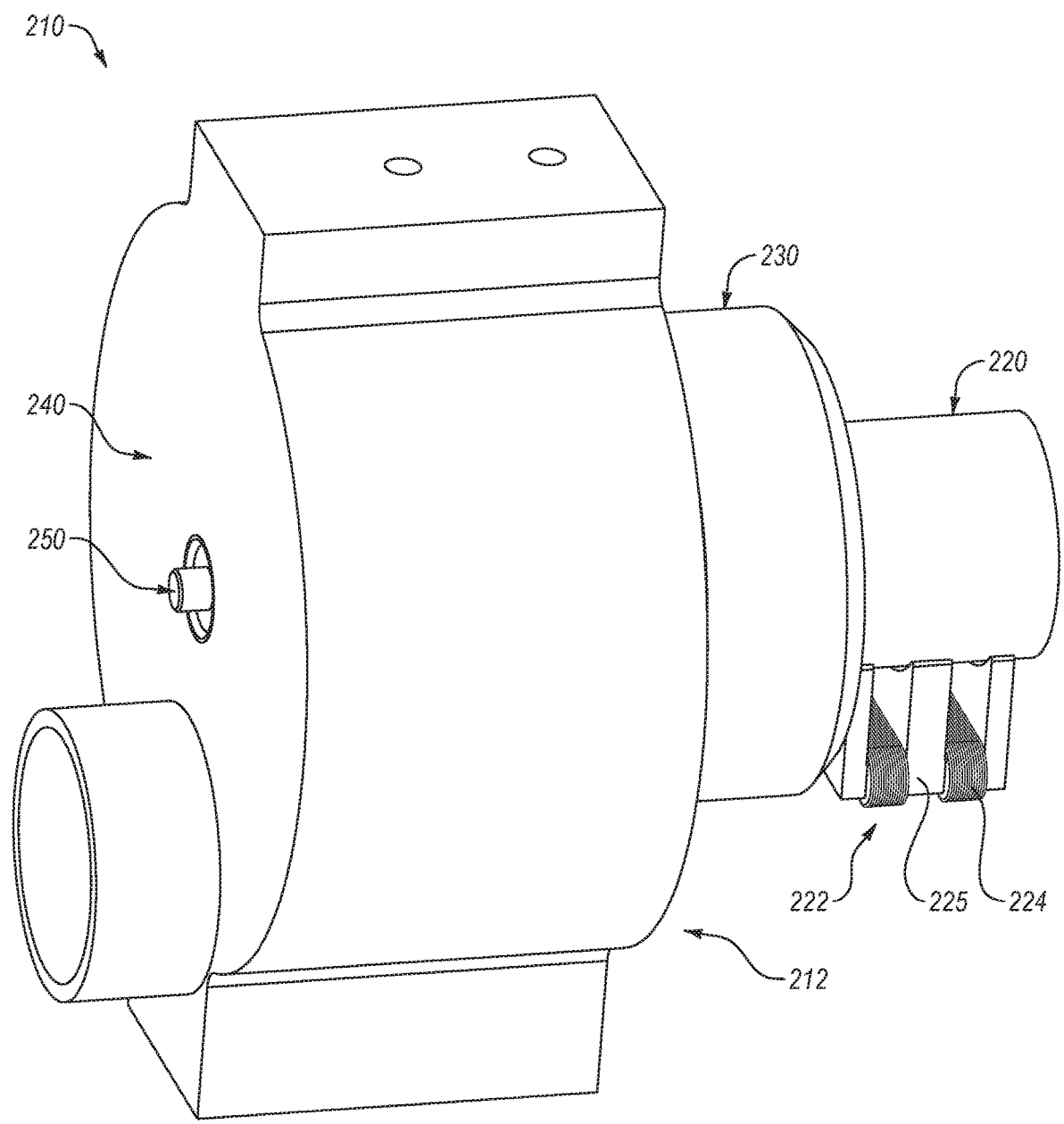
FIG. 3A illustrates a perspective view of another example of an X-ray source.

FIG. 3A illustrates a perspective view of the X-ray source 210. As shown in FIG. 3A, the X-ray source 210 may include an envelope, also referred to as an insert, 212 that includes a wall (e.g., insert wall, vacuum wall or vacuum envelope wall) that encloses the cathode and anode in an evacuated enclosure (or vacuum envelope). The insert 212 may enclose an anode assembly 240, a bearing assembly 250, a motor assembly 230 and a lift assembly 220. The lift electromagnet 222 may include a lift electromagnet core 225 with three poles formed in an "M" or "W" shape with windings (or coils or wires) 224 wrapped around the core 225 between the poles as shown, or around the poles.

Figure 3B:
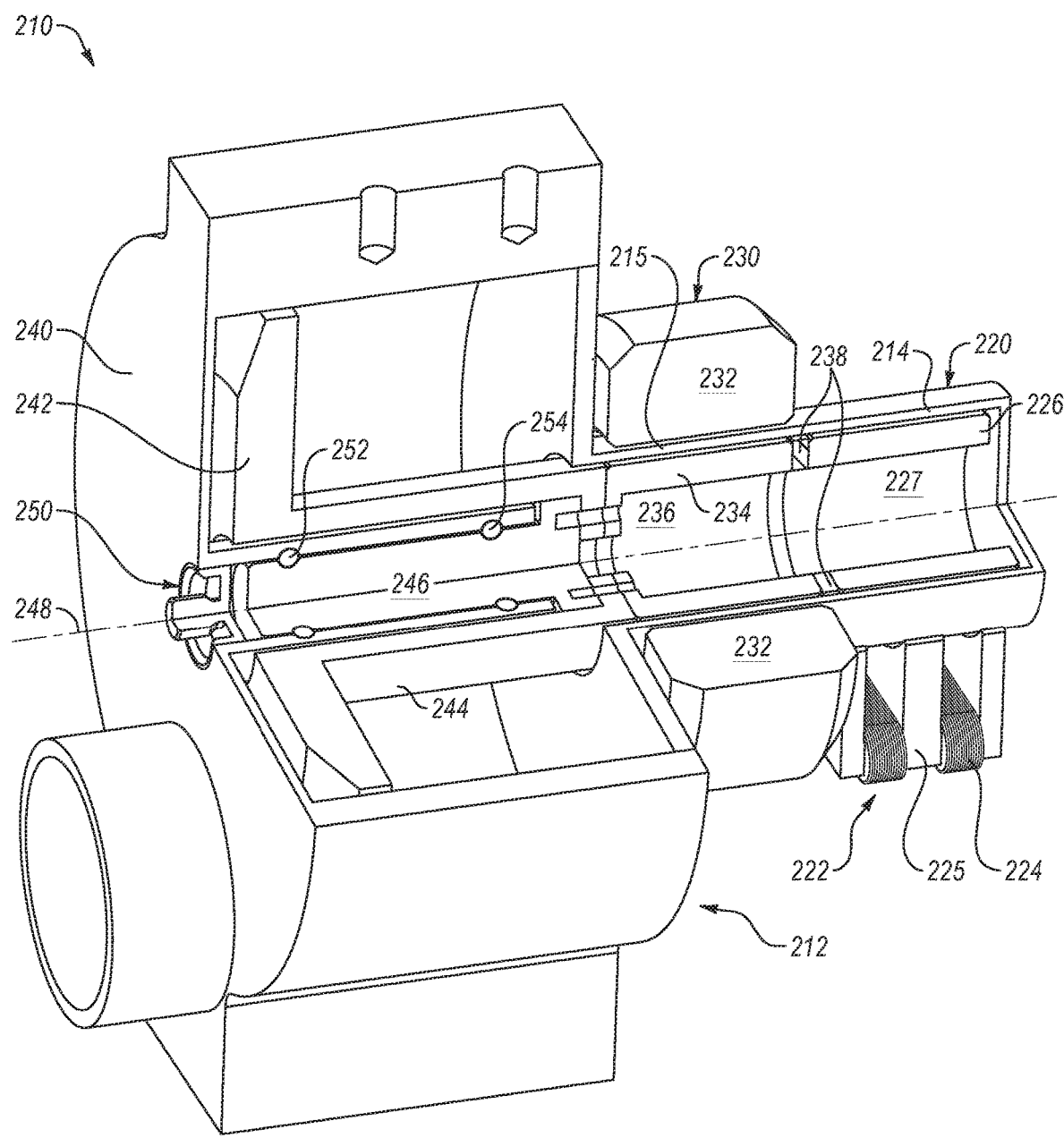
FIG. 3B illustrates a perspective section view of the X-ray source of FIG. 3A.
Figure 3C:
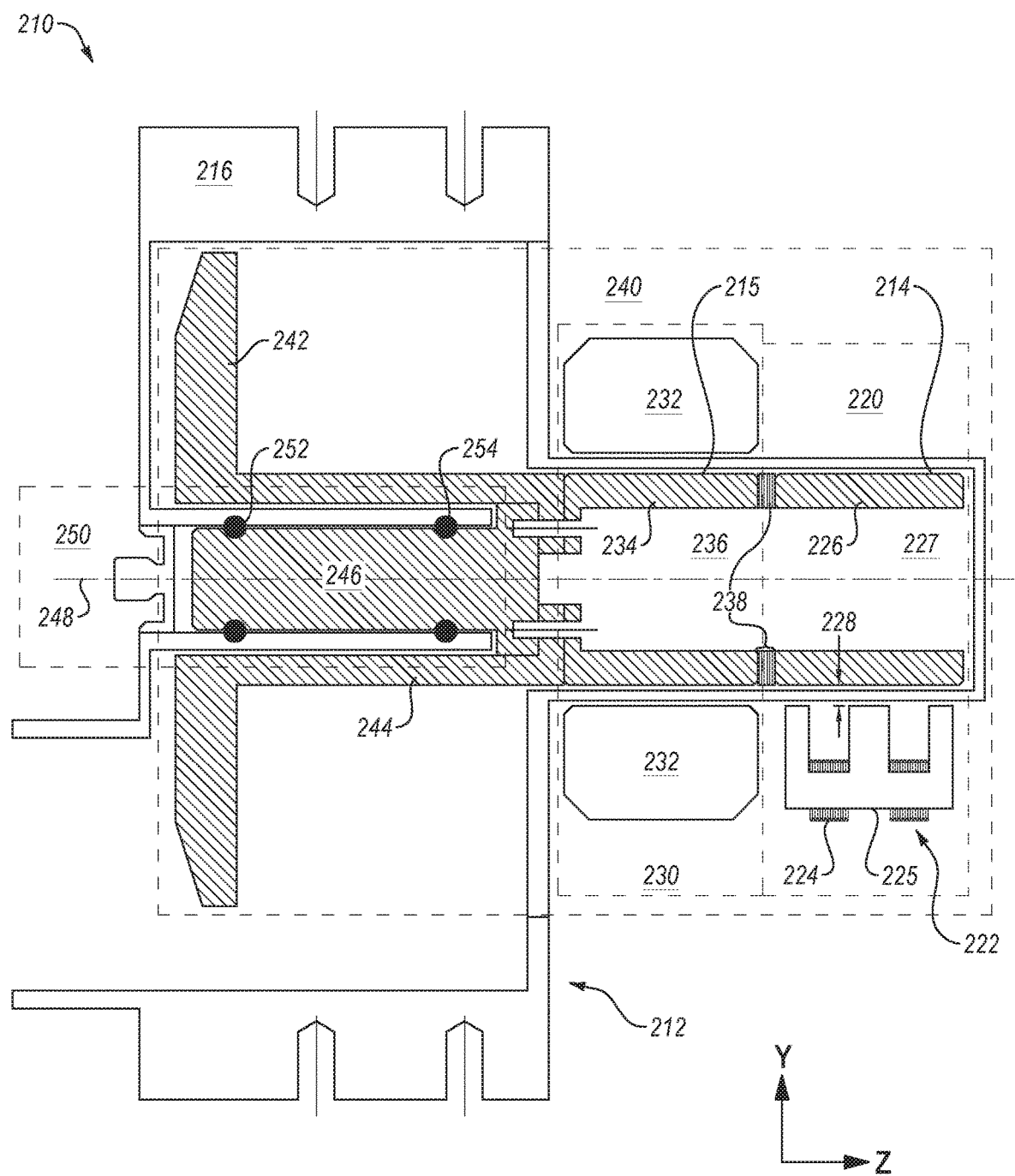
FIG. 3C illustrates a side cross section view of the X-ray source of FIG. 3A.
Figure 3D:
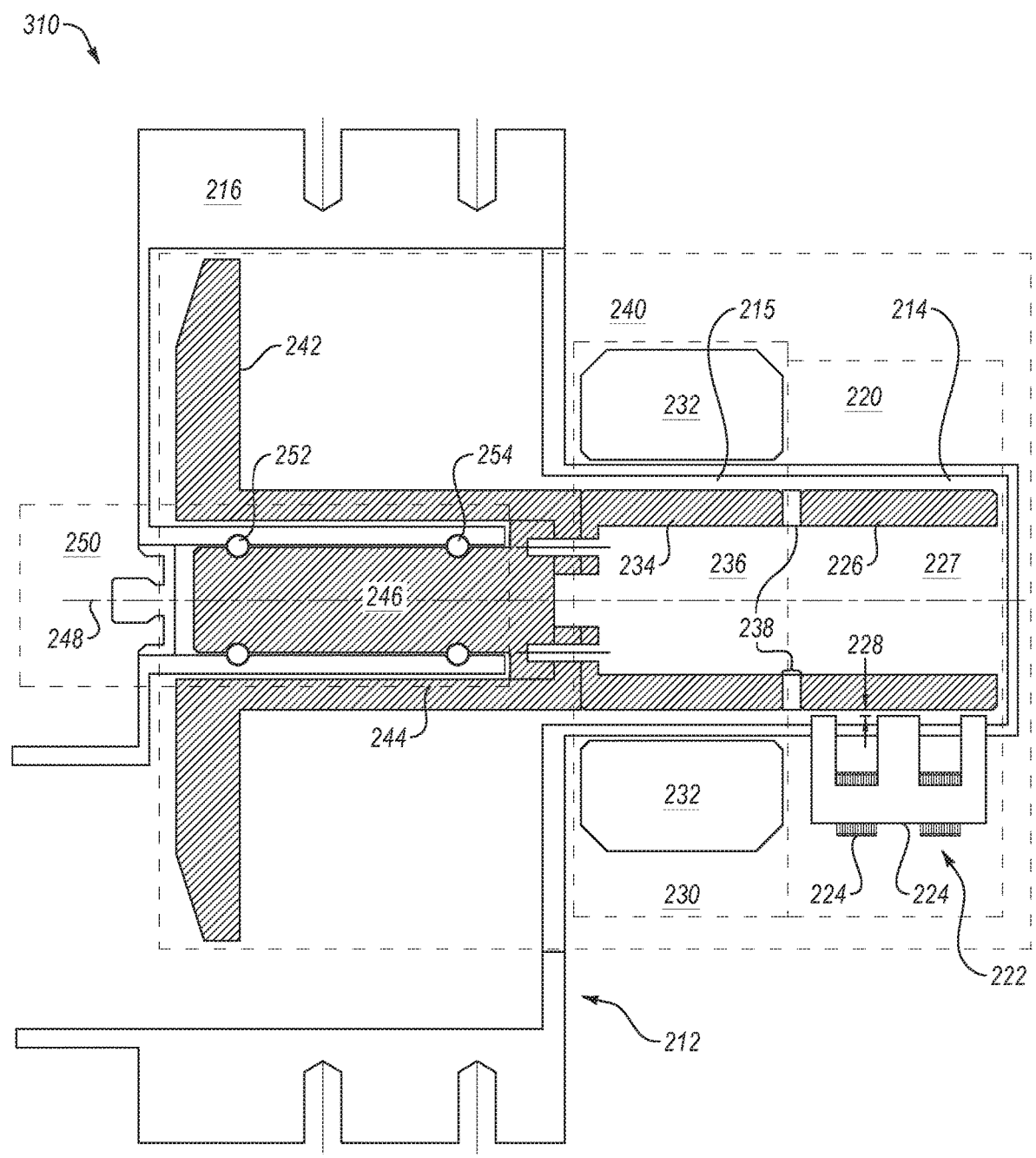
FIG. 3D illustrates a side cross section view of another example of an X-ray source.
Figure 3E:
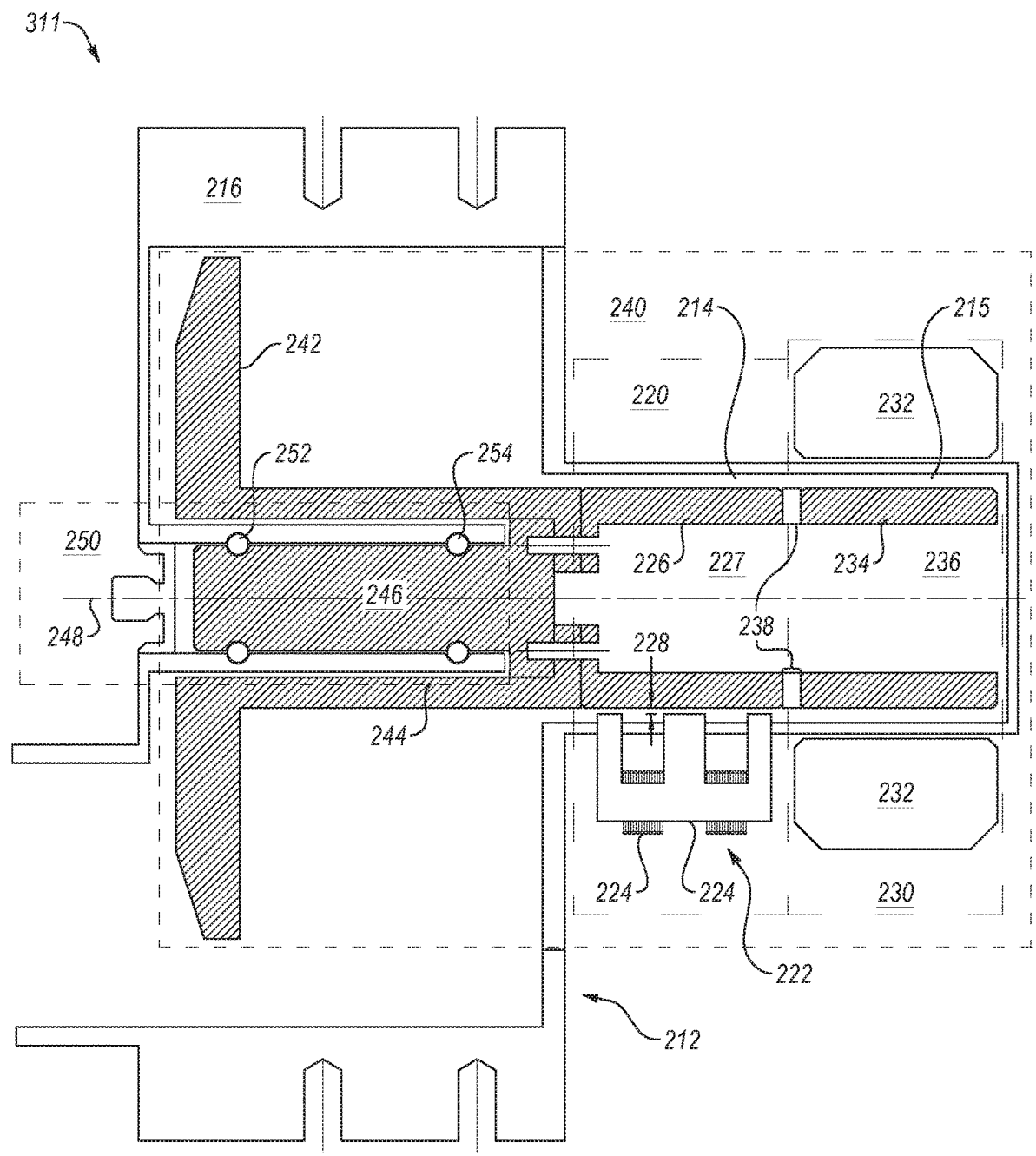
FIG. 3E illustrates a side cross section view of another example of an X-ray source.

FIG. 3B illustrates a perspective section view of the X-ray source 210 and FIG. 3C illustrates a side cross section view of the X-ray source 210. As shown in FIGS. 3B-3C, the anode assembly 240, the bearing assembly 250, the motor assembly 230, and lift assembly 220 may facilitate rotation about an anode assembly centerline (or bearing centerline) 248. The anode assembly 240 includes an anode 242 and an anode outer shaft 244 that supports the anode 242. The anode assembly 240 also includes an anode inner shaft 246 that is coupled to the anode outer shaft 244 and rotatably coupled to the bearings 252 and 254 of the bearing assembly 250.

The anode inner shaft 246 may include at least one bearing race (e.g., ball bearing race). For example, in the illustrated configuration the bearing assembly 250 includes the outer ball bearing 252 and a corresponding race on the anode inner shaft 246, and an inner ball bearing 254 and a corresponding race. As used herein, outer refers to a relative position closer to an edge of the anode assembly 240, closer to the anode 242, or further away from the motor assembly 230. Inner refers to a position closer to a middle of the anode assembly 240, further away from the anode 242, or closer to the motor assembly 230.

Although the illustrated embodiment includes a roller element bearing (e.g., tool steel ball bearing or tool steel raceways), in other embodiments other bearing types may be implemented. For example, other configurations may include plain bearings (e.g., a sleeve bearing or a journal bearing), or hydrodynamic bearings, such as liquid metal bearings. U.S. patent application Ser. No. 14/968,078, filed Dec. 14, 2015, entitled, "Antiwetting Coating for Liquid Metal," which is hereby incorporated by reference in its entirety, discloses an example of a liquid metal bearing.

The motor assembly 230 may include a stator 232 and a rotor 234. The rotor 234 includes a rotor void 236 or opening on one end, which may be cylindrical. The rotor void 236 allows the rotor 234 to be attached to the anode shaft (e.g., the anode inner shaft 246) and/or aligned with the bearing centerline 248. The components (e.g., the anode shaft, the rotor 234, or the rotor shaft) may be attached to each other using a permanent or semi-permanent fastening or attachment mechanisms. An insert wall 215 (or a portion of the insert wall) proximate the motor assembly 230 may be disposed between the rotor 234 and the stator 232. The electromagnetic induction from the magnetic field of winding of the stator 232 may pass through the insert wall 215 to the rotor 234. A small gap between the insert wall 215 and the rotor 234 allows the rotor 234 to rotate without mechanical resistance.

The lift assembly 220 includes the lift shaft 226 coupled to the rotor 234 and the lift electromagnet 222 that may apply a magnetic force on the lift shaft 226. The lift shaft 226 may include a lift shaft void 227 or an opening, which may be cylindrical. A rotor-to-lift shaft adapter 238 may couple the rotor 234 to the lift shaft 226. The rotor-to-lift shaft adapter 238 can include a non-ferromagnetic material to improve magnetic isolation between the motor assembly 230 and the lift assembly 220 which both use magnetic fields for operation. In non-illustrated configurations, the lift shaft 226 may be integrated with or permanently attached (e.g., welded or brazed) to the rotor 234.

The lift electromagnet 222 may include at least two poles that are oriented towards the lift shaft 226. In some configurations, the lift electromagnet 222 may include three poles (tri-pole) formed in an "M" or "W" shape with windings 224 wrapped around the core 225 (or a core web) between the poles.

Material choices may affect the performance of a magnetic device, such as the lift electromagnet 222 or the lift shaft 226. Magnetic material needs to stay magnetized in vacuum (e.g., the vacuum envelope of an X-ray source) and after processing and be vacuum compatible, such as cold drawn carbon magnetic iron (CMI-C).

The lift electromagnet 222 or the lift shaft 226 may include ferromagnetic and/or ferrimagnetic materials. As used herein and for simplicity in describing the technology, a "ferromagnetic" material refers to a material that can exhibit spontaneous magnetization (i.e., either a ferromagnetic material or a ferrimagnetic material).

The windings 224 around the core 225 may include an electrical conductive material (e.g., copper or aluminum) with an electrically insulated sheath, such as enameled magnet wire (i.e., transformer wire or Litz wire).

Two factors that can reduce the lift force between the lift shaft 226 and the lift electromagnet 222 are the size of the lift gap and the presence of interstitial materials such as the insert wall with magnetic permeability greater than 1. As shown in FIG. 3C, a lift gap 228 may be the spacing between the lift shaft 226 and the lift electromagnet 222. The lift gap 228 may include the insert wall 214 proximate the lift assembly 220 along with a vacuum between the insert wall 214 and the lift shaft 226. In some examples, the lift gap 228 may include the space between the insert wall 214 and the lift electromagnet 222 when the lift electromagnet 222 does not touch the insert wall 214, such as when the lift electromagnet 222 and the insert wall 214 have different electrical potentials. The lift gap 228 that includes the vacuum provides clearance for the lift shaft 226 to rotate without mechanical resistance (e.g., friction from touching the insert wall 214 or the lift electromagnet 222).

Vacuum and air have a relative magnetic permeability (represented by $\mu_r$), of 1, thus minimizing the dampening of the electromagnetic coupling between the electromagnet shaft 226 and the lift electromagnet 222. The insert wall 214 is typically made of a conductive material with a magnetic permeability >1 such that it increases the dampening of the electromagnetic coupling between the lift electromagnet 222 and the lift shaft 226 reducing the lift force.

The lift assembly 220 may apply a magnetic lift force on the rotating assembly (via the lift shaft 226), which can, for example, improve the operating lifespan and/or increase the load bearing capability of the bearing assembly 250 and components thereof. The magnetic force of the lift electromagnet 222 may be used to counteract loads on the bearing assembly 250, such as the centrifugal force of the gantry (e.g., the gantry 200), as well as to dampen vibration and add stability to the anode assembly (e.g. anode assembly 240) or other rotating components of the X-ray source. The forces generated by the lift assembly 220 may be applied anywhere on the rotating assembly including at the center of mass (or not at the center of mass) and may employ one or a combination of magnetic lift devices that provide the forces.

As mentioned, X-ray tubes generate heat during operation. For example, when electrons strike the focal track or target of an anode, the kinetic energy of the electrons create heat. Additionally or alternatively, bearing assemblies, electromagnet lift assemblies and/or motor assemblies may generate heat via friction and/or Joule heating, although the amount of heat may be less than the heat generated from electrons striking the anode. The heat generated may need to be dissipated to avoid thermally stressing X-ray tube components.

Accordingly, X-ray tubes may include features to dissipate heat. For example, rotating disc-shaped anodes may be implemented to spread the heat generated by the electron beam across a larger area. A fluid coolant such as a liquid or air may fill a space or cavity between the housing and the insert defining the evacuated envelope to dissipate heat generated by the X-ray tube. The coolant fluid may surround and cool various portions of the X-ray tube, such as the insert and motor stator. In some configurations, the coolant fluid may be a dielectric oil or other suitable coolant. Additionally or alternatively, X-ray tubes may include heat exchangers, to dissipate heat from the coolant fluid to an exterior of the X-ray tube.

When lift assemblies are incorporated into X-ray tubes to counter balance forces on rotating components resulting from gantry rotation in CT systems, the lift assemblies may also generate heat that may need to be dissipated. To generate the required lift force to counter balance gantry rotation forces, lift electromagnets may require relatively high current passing through its core or windings. In one example, a current of 5 amperes (A) or larger may be passed through the windings of a lift electromagnet. This current may heat up the windings, in some circumstances generating 500 watts (W) or more of heat. If the heat generated by the lift electromagnet is not suitably dissipated, it may compromise various components of the lift assembly and/or the X-ray tube. For example, electrical insulation (e.g., around the windings) or other electrical wiring may be damaged by excessive heat. In another example, the coolant (e.g., a dielectric oil) surrounding the insert of the X-ray tube may break down and fail when exposed to excessive heat. Accordingly, the heat generated by the lift assembly may need to be dissipated for the lift assembly and the X-ray tube to operate properly.

Accordingly, disclosed embodiments include example configurations to dissipate heat generated by the lift electromagnet. For example, in some embodiments the lift electromagnet may be cooled by a coolant, such as a dielectric oil, that surrounds the lift electromagnet. In some configurations the coolant that cools the lift electromagnet may be the same coolant that cools the other portions of the X-ray tube (e.g., the anode, bearing assembly and/or motor assembly) and may be positioned between the housing and the insert of the X-ray tube.

In addition, disclosed embodiments include example configurations to increase heat dissipation from the lift electromagnet to the coolant referred to herein as heat dissipating structures, thermal dissipating structures, cooling structures, or heat transfer structures. For example, materials with relatively high heat conductivity may be implemented at the interfaces of various components to increase heat dissipation. In another example, the surface area of certain components, such as the windings or the core of the lift electromagnet, may be increased to improve heat dissipation.

Furthermore, disclosed heat dissipating structures include configurations to direct the coolant around the lift electromagnet to improve the flow of coolant proximate the lift electromagnet, thereby improving cooling. Some example configurations implement free convention to direct the flow of coolant proximate the lift electromagnet. In such configurations, the force of the rotation of the gantry may direct the coolant to flow proximate the lift electromagnet. Fins or thin thermally conductive planar structures may be oriented in a manner to increase heat dissipation as the coolant is driven by coolant flow or the centrifugal force of the rotating gantry. In other configurations, forced convection may be implemented to direct the flow of coolant proximate the lift electromagnet. In such configurations, fins may be oriented in a manner to increase forced convection heat dissipation as the coolant is driven proximate the lift electromagnet.

Figure 4A:
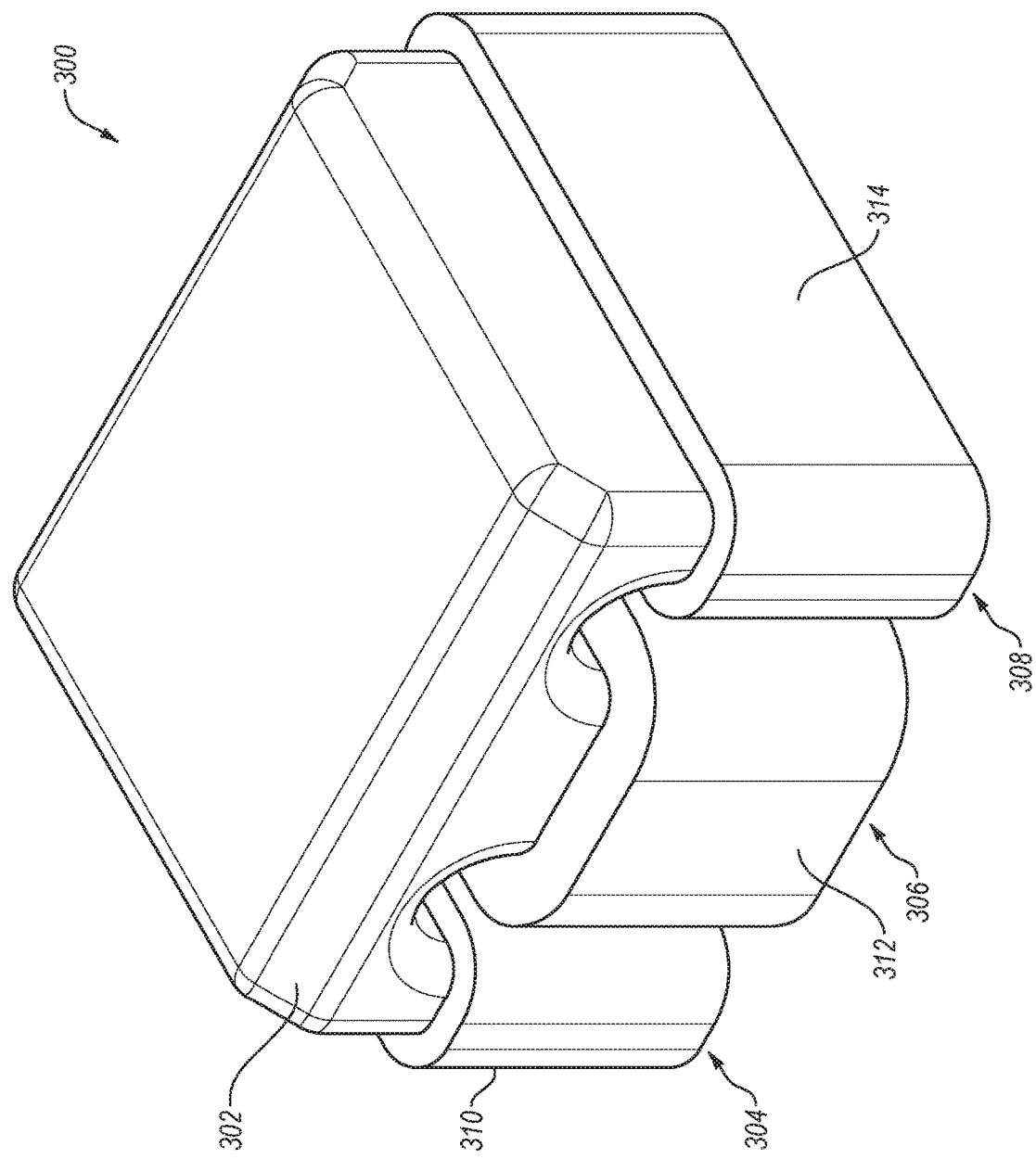
FIG. 4A illustrates a perspective view of an example of a lift electromagnet that may be implemented in an X-ray tube.

FIG. 4A illustrates a perspective view of an example of a lift electromagnet 300. The lift electromagnet 300 may include suitable aspects described with respect to the lift electromagnet 222 of FIG. 3C, such as a core 302 and with three poles 304, 306, 308. Windings 310, 312, and 314 may be wrapped around the core 302 between the poles 304, 306, 308. The windings 310, 312, 314 may include an electrical conductive material (e.g., copper, aluminum or another suitable conductive material) with an electrically insulated sheath, such as a polymer (e.g., polymide, or another suitable insulating material).

Figure 4B:
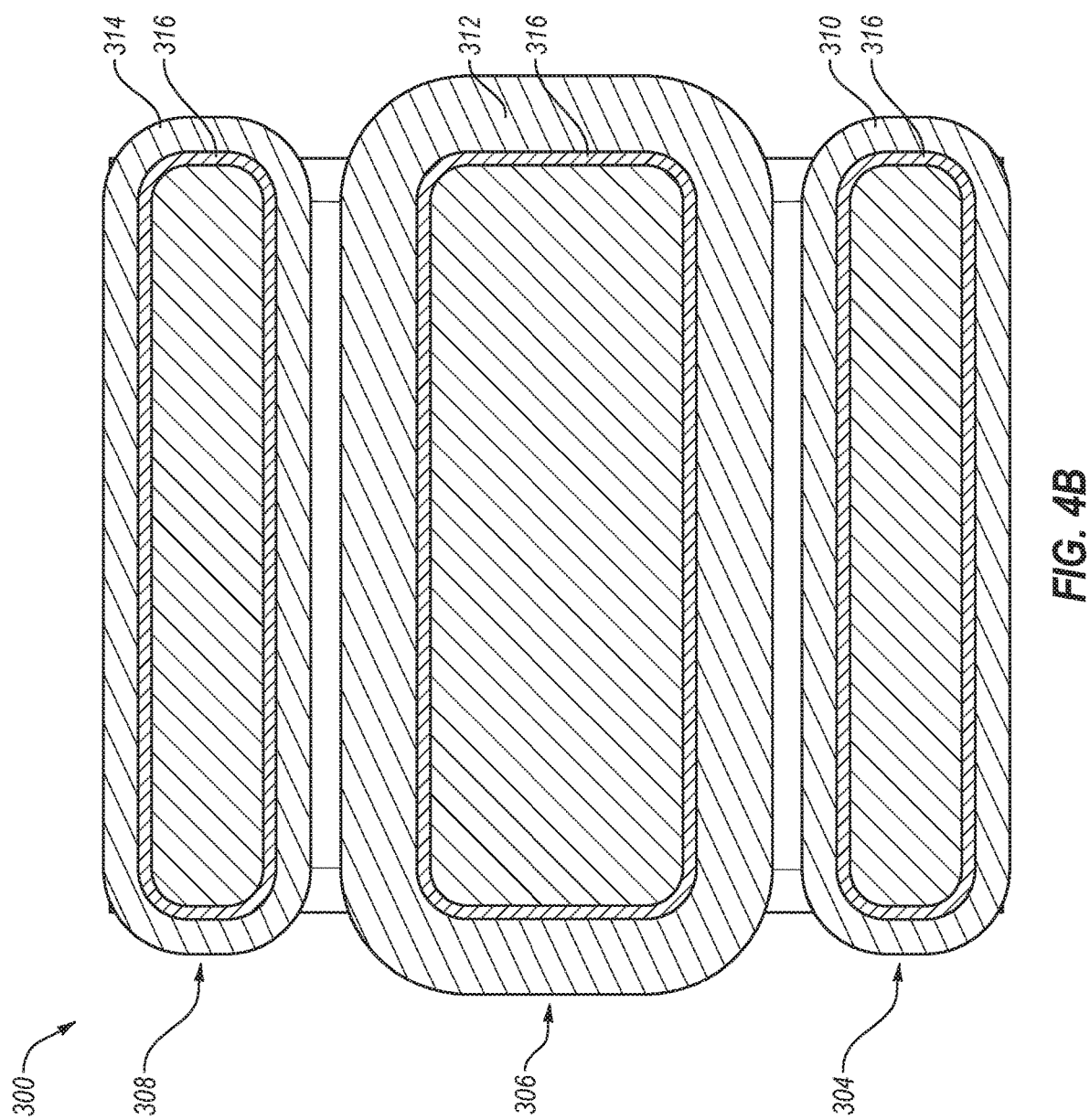
FIG. 4B illustrates a bottom section view of the lift electromagnet of FIG. 3D.

FIG. 4B illustrates a bottom section view of the lift electromagnet 300. As illustrated, a thermal interface 316 may be positioned between the windings 310, 312, 314 and the poles 304, 306, 308 (or the core 302 proximate the poles 304, 306, 308). The thermal interface 316 may include a material with a relatively high thermal conductivity, and may facilitate the transfer of heat away from the windings 310, 312, 314 during operation. Although not shown, the thermal interface 316 may also be positioned around the windings 310, 312, 314 or other portions of the lift electromagnet 300. In some configurations, the thermal interface 316 may be positioned on an external surface of the lift electromagnet 300 or the windings 310, 312, 314.

The thermal interface 316 may facilitate the transfer of heat to the core 302 which may act as a heat sink during operation of the lift electromagnet 300 (e.g., as the gantry is rotating). In some configurations, the relatively large thermal mass of the core 302 may store heat generated at the windings 310, 312, 314 during operation of the lift electromagnet 300. The stored heat may transfer to the coolant (e.g., to the coolant surrounding the lift electromagnet 300) after the lift electromagnet 300 is turned off. In particular, the heat may transfer to the coolant in between scans, when the gantry is not rotating and therefore the lift electromagnet 300 does not need to be operating. Additionally or alternatively, the thermal interface 316 may facilitate the transfer of heat from the windings 310, 312, 314 and the core 302 to the coolant. The thermal interface 316 may facilitate heat dissipation by increasing the thermal contact area between different components.

The thermal interface 316 may include a solid or liquid material that has a relatively high thermal conductivity. In some configurations the thermal conductivity of the thermal interface 316 may be higher than the thermal conductivity of the coolant (e.g., a dielectric oil). Additionally or alternatively, the thermal interface 316 may include a material that conforms to the surface of the windings 310, 312, 314 and the core 302 (i.e., a "conformable material"), thereby forming a good thermal contact with a sufficiently large surface area. Since the thermal interface 316 may at least partially contact the coolant in some areas, the material of the thermal interface 316 may be selected so it does not break down in the coolant and/or does not release material into the coolant that may contaminate the coolant.

In some configurations, the thermal interface 316 may be a thermal grease, epoxy, filler, or potting material with a relatively high thermal conductivity. In other configurations, the thermal interface 316 may be a foil with a relatively high thermal conductivity. For example, the thermal interface 316 may include a material with a thermal conductivity of at least 0.5 W/(m·K) between 50 W/(m·K) and 200 W/(m·K) between 50 W/(m·K) and 500 W/(m·K), or between 50 W/(m·K) and 2200 W/(m·K). The thermal interface 316 may include a material such as copper, gold, silver, diamond, boron nitride, aluminum or other suitable materials.

The thermal interface 316 may be positioned or formed using any suitable technique. For example, the thermal interface 316 may be positioned around the poles 304, 306, 308 before the windings 310, 312, 314 are wound around the core 302. In another example, the thermal interface 316 may be injected as a liquid or viscoelastic solid in a position between the windings 310, 312, 314 and the core 302. Gas or air pockets may be removed via evacuation or another suitable manner. The thermal interface 316 may then be cured or allowed to solidify.

Figure 5:
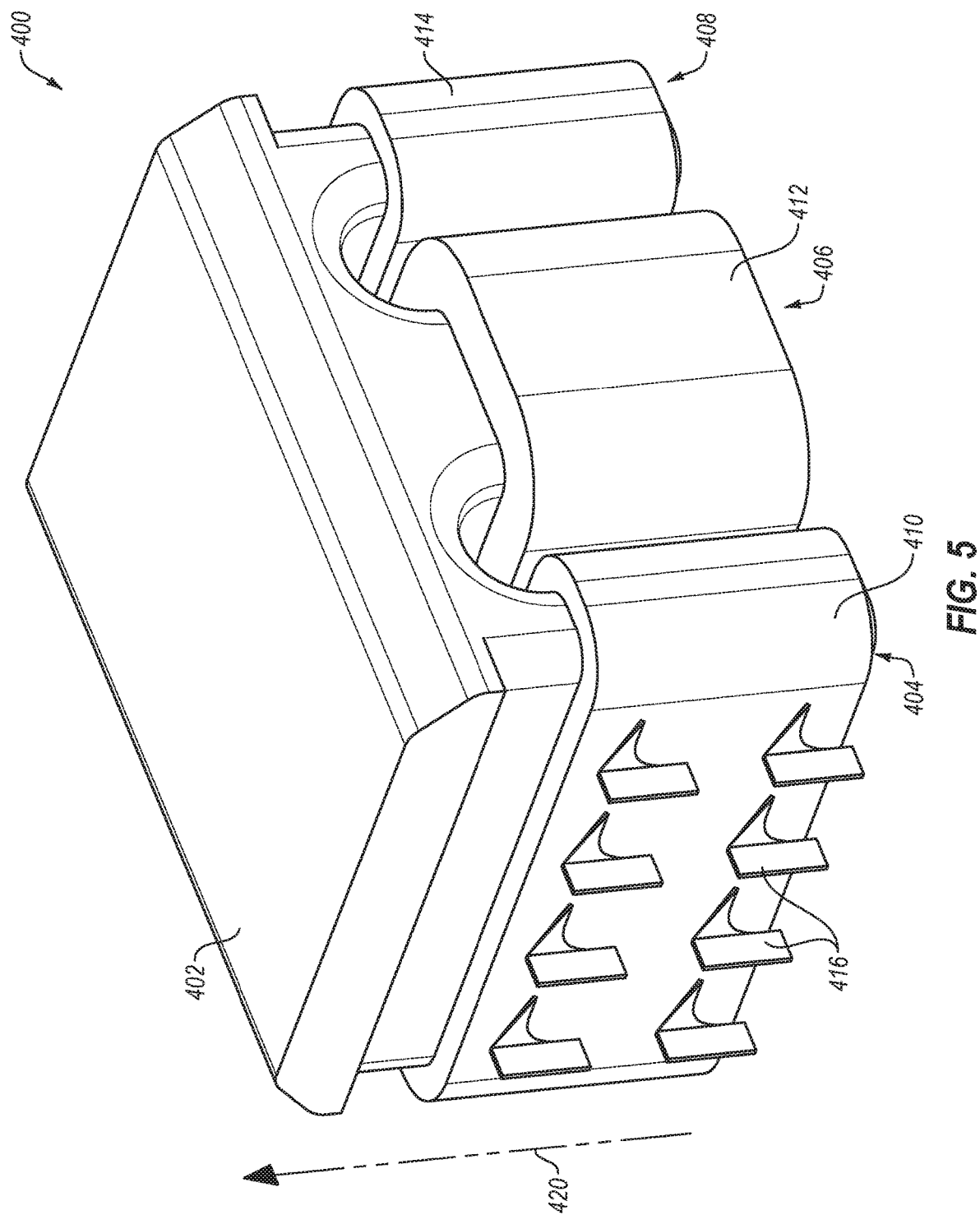
FIGS. 5-6 illustrate perspective views of another example of a lift electromagnet that be implemented in an X-ray tube.
Figure 6:
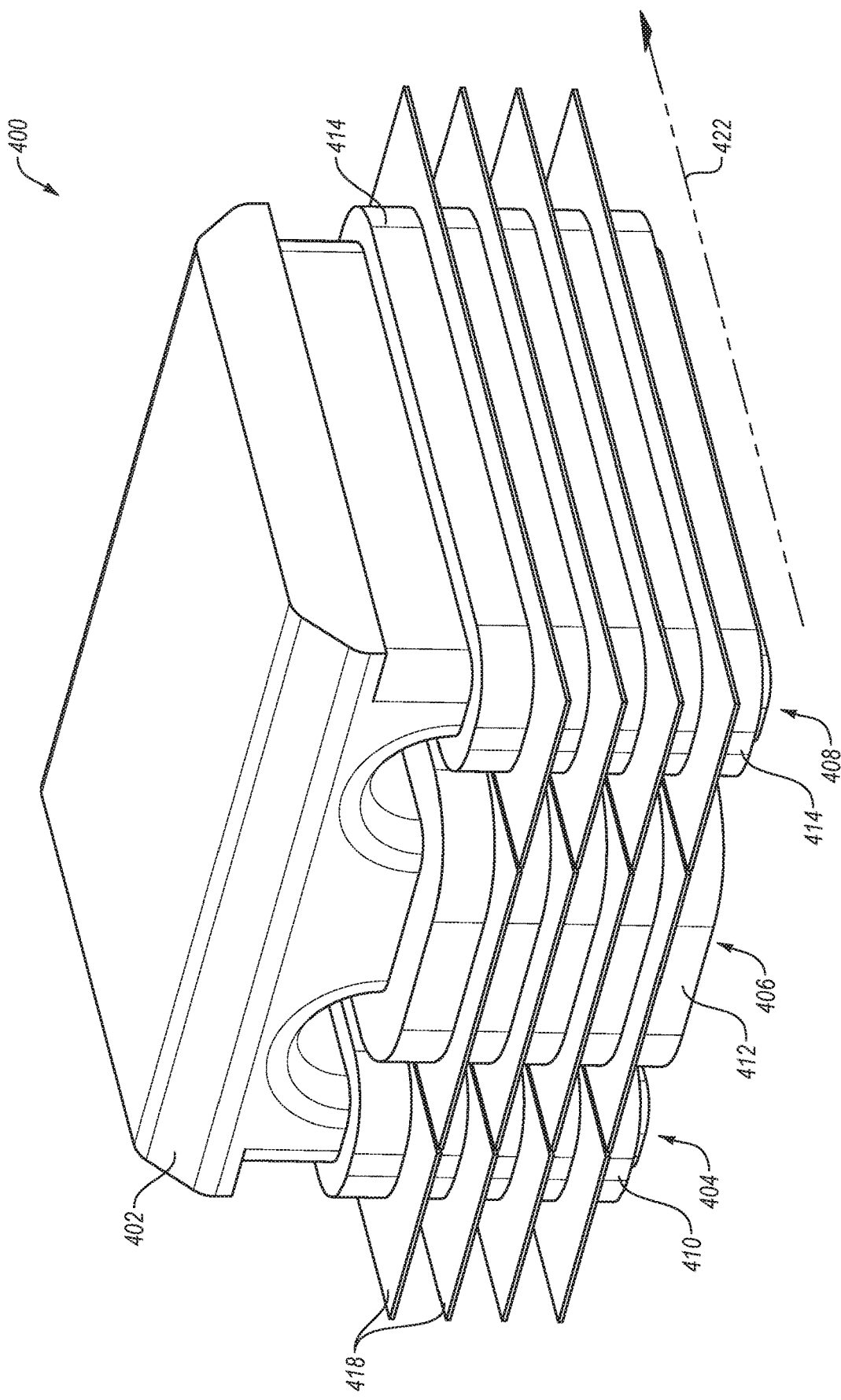

FIGS. 5 and 6 illustrate perspective views of another example of a lift electromagnet 400. The lift electromagnet 400 may include suitable aspects described with respect to the lift electromagnet 222 of FIG. 3C and/or the lift electromagnet 300 of FIG. 4A. In particular, the lift electromagnet 400 includes a core 402 and with three poles 404, 406, 408. Windings 410, 412, and 414 may be wrapped around the core 402 between the poles 404, 406, 408.

As shown in FIG. 5, the lift electromagnet 400 may include protrusions or fins 416 (e.g., thin thermally conductive planar structures) positioned on one or more of the windings 410, 412, and 414. Although FIG. 5 shows the fins 416 positioned on the pole 404, the other poles 406, 408 may also include the fins 416. Additionally or alternatively, as shown in FIG. 4B, the lift electromagnet 400 may include protrusions or fins 418 positioned on or between one or more of the windings 410, 412, and 414.

In some configurations, the fins 416 or 418 may be inserted into the windings 410, 412, and 414. For example, the fins 416, 418 may be inserted in between adjacent windings 410, 412, and 414 or interwoven with the windings 410, 412, and 414. In other configurations, the fins 416, 418 may be coupled to the windings 410, 412, and 414 using any suitable adhesive or fastening mechanism. In configurations where the lift electromagnet 400 includes a thermal interface, such as a thermal grease, epoxy, potting material or filler, the fins 416, 418 may be inserted into or coupled with the thermal interface. Additionally or alternatively, the fins 416, 418 may be formed of the thermal interface material. In particular, the fins 416, 418 may be molded or otherwise formed from potting material or filler.

The fins 416, 418 may include a material that has a relatively high thermal conductivity. For example, the fins 416, 418 may include a material with a thermal conductivity of at least 0.5 W/(m·K), between 50 W/(m·K) and 200 W/(m·K), between 50 W/(m·K) and 500 W/(m·K) or between 50 W/(m·K) and 2200 W/(m·K). In some configurations, the fins 416, 418 may include a material such as copper, gold, silver, diamond, boron nitride, aluminum or other suitable materials. The fins 416, 418 may increase the surface area through which heat may travel from the lift electromagnet 400 to the surrounding coolant.

In the configuration of FIG. 5, a coolant flow, denoted by 420, may be caused by the rotation of the gantry and may cause the coolant to flow in a direction parallel to the centrifugal force along the lift electromagnet 400 (or perpendicular to the lift shaft, or the axis of rotation of the anode or the lift shaft). The direction of the centrifugal force may be perpendicular to an axis of rotation of the gantry. Such configurations may be referred to as free convection configurations, because the coolant flows freely around the lift electromagnet 400.

In such configurations, the fins 416 may be shaped and positioned to extend parallel to the centrifugal force (or perpendicular to the lift shaft, or the axis of rotation of the anode or the lift shaft), and therefore parallel to the coolant flow 420. In particular, the largest or longest dimension of the fins 416 may be parallel to the centrifugal force 420 and/or the flow of coolant. In such configurations, the coolant may flow over the fins 416 to remove heat, and the surface area of the fins 416 exposed to the flowing coolant may be maximized to facilitate free convection cooling of the lift electromagnet 400.

In some configurations, the coolant may flow freely as a result of the centrifugal force 420. In other configurations, the coolant may be forced to flow in a certain direction around the lift electromagnet 400, rather than flowing freely as a result of the centrifugal force 420. Similarly, as illustrated in FIG. 6 the coolant may be directed to flow in a direction 422. Such configurations may be referred to as forced convection configurations, because the coolant is directed around the lift electromagnet 400 in a specific direction. However, in other configurations the coolant may flow freely as a result of the centrifugal force or other forces. In the illustrated configuration, the direction 422 is perpendicular to the centrifugal force caused by the rotation of the gantry. Additionally or alternatively, direction 422 may be parallel to an axis of rotation of an anode or a lift shaft. Furthermore, the direction 422 may be parallel to the channels defined in between the poles 404, 406, 408. However, in other forced convection configurations, the coolant may be directed in any suitable direction around the lift electromagnet 400.

As shown in FIG. 6, the fins 418 may be shaped and positioned to extend substantially parallel to the direction 422 of coolant flow, and substantially perpendicular to the centrifugal force caused by the rotation of the gantry (or parallel to the lift shaft, or the axis of rotation of the anode or the lift shaft). In particular, the largest or longest dimension of the fins 418 may be generally parallel to the direction 422 and/or the flow of coolant. In such configurations, the coolant may flow over the fins 418 to remove heat, and the surface area of the fins 418 exposed to the flowing may be maximized to facilitate forced convection cooling of the lift electromagnet 400.

As shown, the fins 418 may be substantially planar and may extend around each of the poles 404, 406, 408. In some configurations, each of the poles 404, 406, 408 is surrounded by multiple dedicated fins 418. For example, each of the fins 418 may be substantially planar with an opening defined to receive one of the poles 404, 406, 408. In other configurations, each of the fins 418 surrounds all of three of the poles 404, 406, 408. For example, each of the fins 418 may be substantially planar with three openings defined to receive each of the poles 404, 406, 408.

In some circumstances, heat transfer for forced convection configurations may be greater than comparable free convection configurations because a larger amount of coolant flows over the fins 418. In particular, the convective heat transfer coefficient for forced convection configurations may be multiple times larger than free convection configurations. In some circumstances, the convective heat transfer coefficient for forced convection configurations may be ten times larger than free convection configurations. Accordingly, forced convection configurations may be preferable in circumstances where large amounts of heat needs to be dissipated and removed. However, forced convection configurations may be more complicated and costly to implement, because components are required to force the coolant in specific directions and to specific areas of the lift electromagnet 400.

Figure 7A:
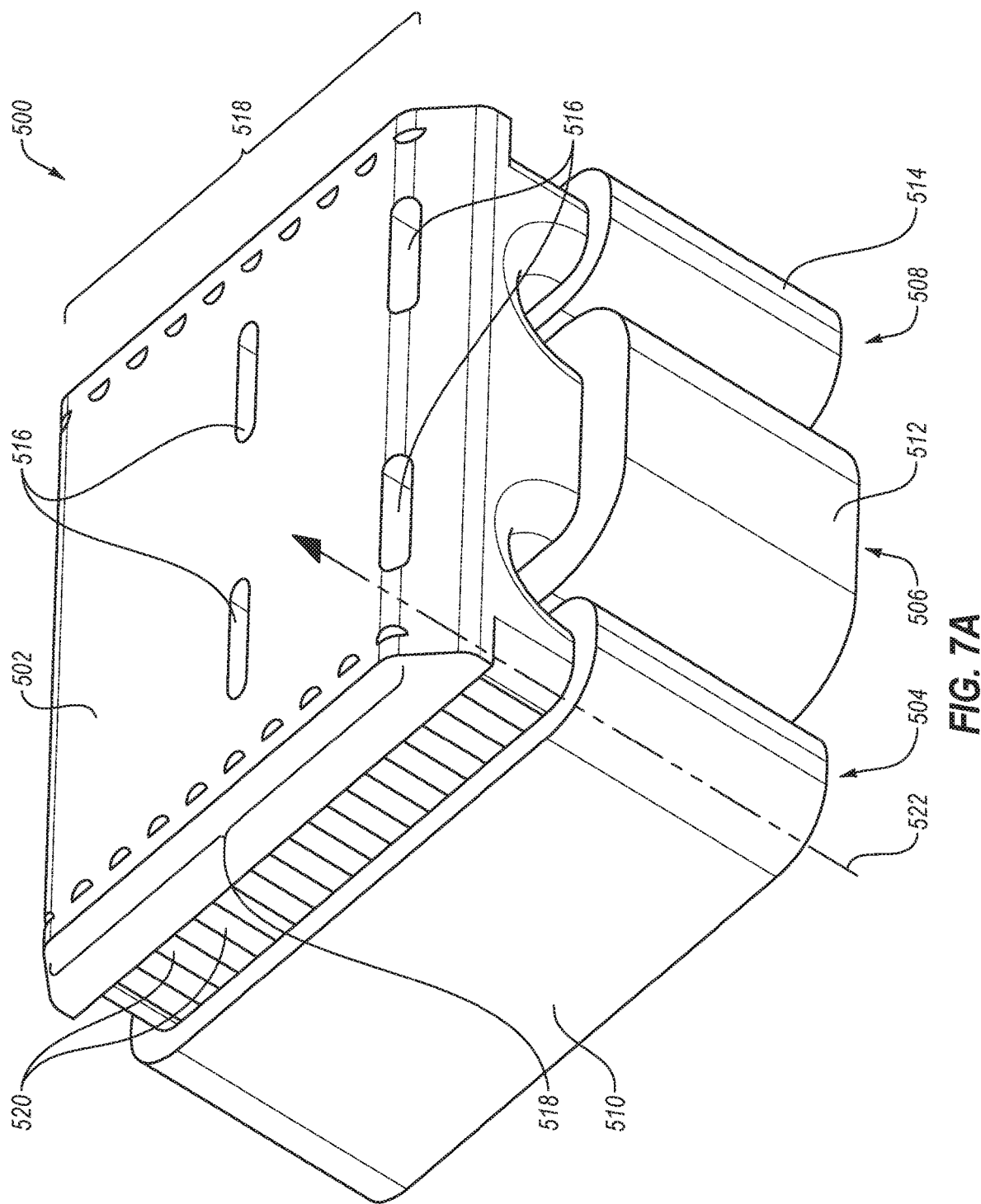
FIG. 7A illustrates a perspective view of another example of a lift electromagnet.

FIG. 7A illustrates a perspective view of another example of a lift electromagnet 500 and FIG. 7B illustrates a top view the lift electromagnet 500. The lift electromagnet 500 may include suitable aspects described with respect to the lift electromagnets described above. In particular, the lift electromagnet 500 includes a core 502 and with three poles 504, 506, 508. Windings 510, 512, and 514 may be wrapped around the core 502 between the poles 504, 506, 508.

As shown, the lift electromagnet 500 may include openings 516 and 518 extending through the core 502. The openings 516 may extend through the top of the core 502 to the spaces in between the poles 504, 506, 508. The lift electromagnet 500 may also include slots or channels 520 positioned on the poles 504, 506, 508 (or extending the length of the poles 504, 506, 508). In some configurations, the channels 520 may extend along the poles 504, 506, 508 and may be defined in the surface of the poles 504, 506, 508. The openings 518 may extend through the top of the core 502 to the channels 520 to permit a coolant to travel in between the channels 520 and the openings 518. Although FIG. 7A shows the channels 520 on the pole 504, it should be appreciated that some or all of the poles 504, 506, 508 may include similar channels. The openings 516, 518 and the channels 520 may be formed by any suitable process, for example, drilling or machining.

In some aspects, FIGS. 7A-7B may be free convention configurations where coolant flows freely around the lift electromagnet 500. In other aspects, forced flow configurations may be implemented to direct coolant around the lift electromagnet 500. A centrifugal force, denoted by 522, caused by the rotation of the gantry may cause the coolant to flow in a direction parallel to the centrifugal force 522 along the lift electromagnet 500. Additionally or alternatively, in some circumstances a coolant may include a thermal gradient, with hotter coolant positioned towards the bottom of the lift electromagnet 500 and cooler coolant positioned towards the top of the lift electromagnet 500. In such circumstances, buoyancy may drive the hotter coolant upwards, parallel to the direction of the centrifugal force 522.

The coolant may travel in between the poles 504, 506, 508 and through the openings 516 to transfer heat from the windings 510, 512, 514 and/or the poles 504, 506, 508. Additionally or alternatively, the coolant may travel along the channels 520 and through the openings 518 to transfer heat from the windings 510, 514 and/or the poles 504, 508. The channels 520 and the openings 516, 518 may permit the coolant to flow parallel to centrifugal force 522 around and/or through the lift electromagnet 500.

In other configurations, the coolant may be forced to flow in a certain direction around the lift electromagnet 500, rather than flowing freely as a result of the centrifugal force 522. In such configurations, a shroud may at least partially surround the lift electromagnet 500 and may include, inlets, outlets, channels and/or openings to direct coolant in specific directions (e.g., perpendicular to the centrifugal force 522) around and/or through the lift electromagnet 500.

The channels 520 and the openings 516, 518 may be configured so as not to compromise the electromagnetic performance of the lift electromagnet 500, and specifically the poles 504, 506, 508 and the windings 510, 512, 514. Accordingly, the channels 520 and the openings 516, 518 may be sized, shaped and positioned to avoid saturation in undesired places in the core 502. For example, as shown in FIG. 7B, the openings 516 are substantially oval, with a longer dimension and a shorter dimension, and the longer dimension is positioned parallel to magnetic flux through the core 502 of the lift electromagnet 500. Additionally or alternatively, the channels 520 may be configured so the cross-sectional area of the poles 504, 506, 508 is not decreased so as to negatively affect the electromagnetic performance of the lift electromagnet 500.

In the free convection configurations described above, the rotation of the gantry may direct the flow of coolant around and through the lift electromagnets. When the gantry is at rest, the X-ray tube and therefore the lift electromagnets may be positioned at the top or the bottom of the gantry, and the force of gravity or buoyancy forces may drive the coolant around and through the lift electromagnets to transfer heat. Accordingly, the free convention configurations may operate to cool the lift electromagnets even in circumstances where the gantry is not rotating. Although in such circumstances the coolant may not flow through the lift electromagnets as rapidly as when the gantry is rotating, and therefore heat will not transfer as quickly.

In some embodiments, the resistance through the windings may be configured to facilitate cooling of the lift electromagnets. Referring to FIGS. 7A-7B as an example, the outer poles 504, 508 and the corresponding windings 510, 514 may be relatively easier to cool than the inner pole 506 and the windings 512. In particular, the outer windings 510, 514 may be exposed to a larger amount of coolant and it may be easier to direct more coolant around the outer windings 510, 514. Accordingly, the outer windings 510, 514 may be configured to have a higher resistance than the inner windings 512. In such configurations, the outer windings 510, 514 may heat up more than the inner windings 512 because of the increased resistance. Additionally or alternatively, a higher gauge wire may be used for the outer windings 510, 514 than the inner windings 512. In such configurations, a diameter of the outer windings 510, 514 may be greater than a corresponding diameter of the inner windings 512. Higher gauge wire may be used for the outer windings 510, 514 because the outer windings 510, 514 are relatively easier to cool when compared to the inner windings 512 because they are positioned at the periphery of the lift electromagnet 300.

In further embodiments a lift electromagnet and its windings may be at least partially surrounded by an electrically non-conductive potting material such as epoxy. Such configurations may eliminate any space in between the windings, and may provide a better heat interface between the windings and a core of the lift electromagnet because the epoxy increases thermal conduction and heat transfer. Additionally or alternatively, such configurations may decrease the likelihood of gas bubbles or other contaminants forming in the coolant due to excessive heat. This in turn may decrease the likelihood of arcing or artifacts caused by gas bubbles. In some aspects, cooling fins or channels may be molded into the potting material to increase heat transfer via convection.

Figure 8A:
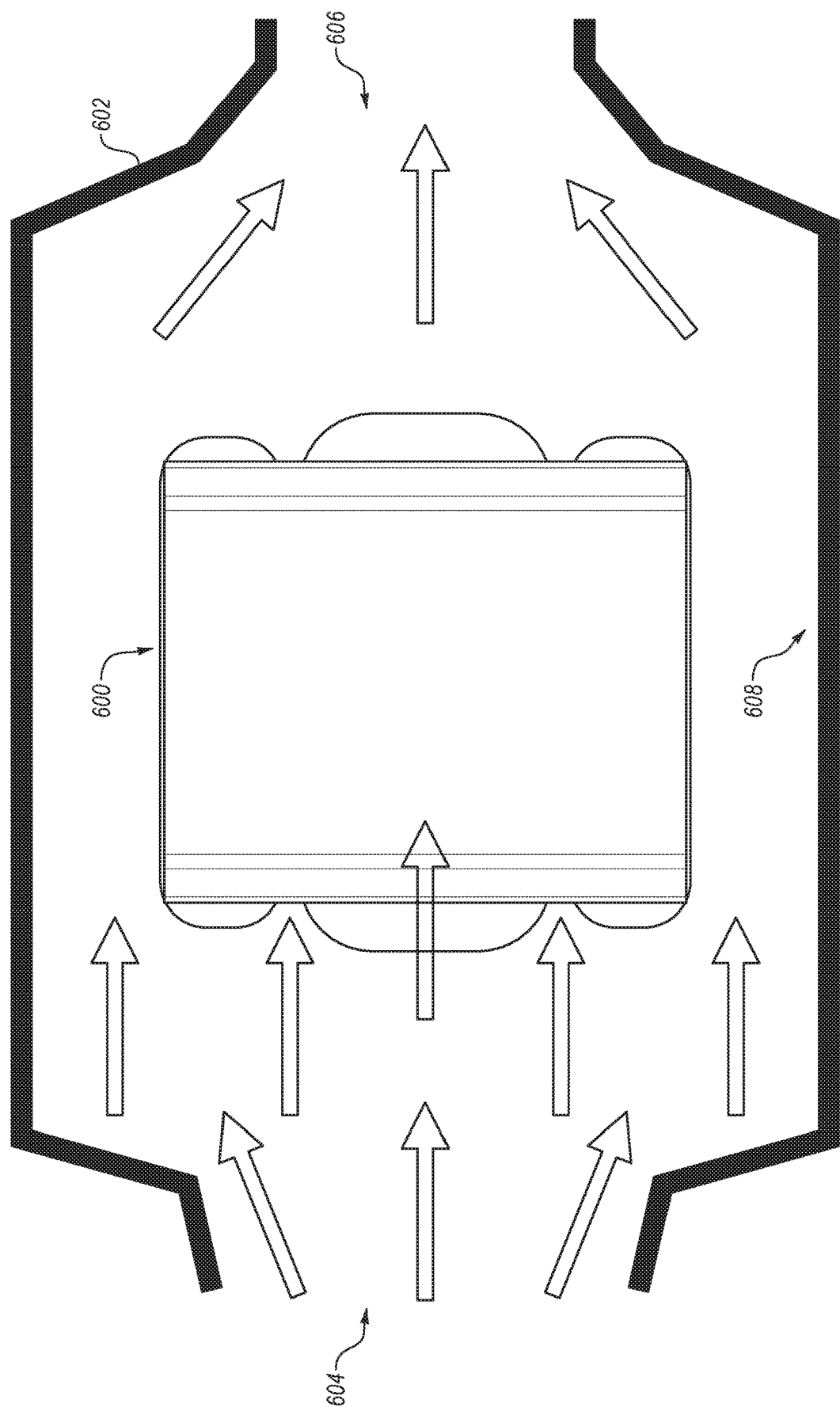
FIG. 8A is a top schematic view of an example shroud that directs flow around a lift electromagnet.
Figure 8B:
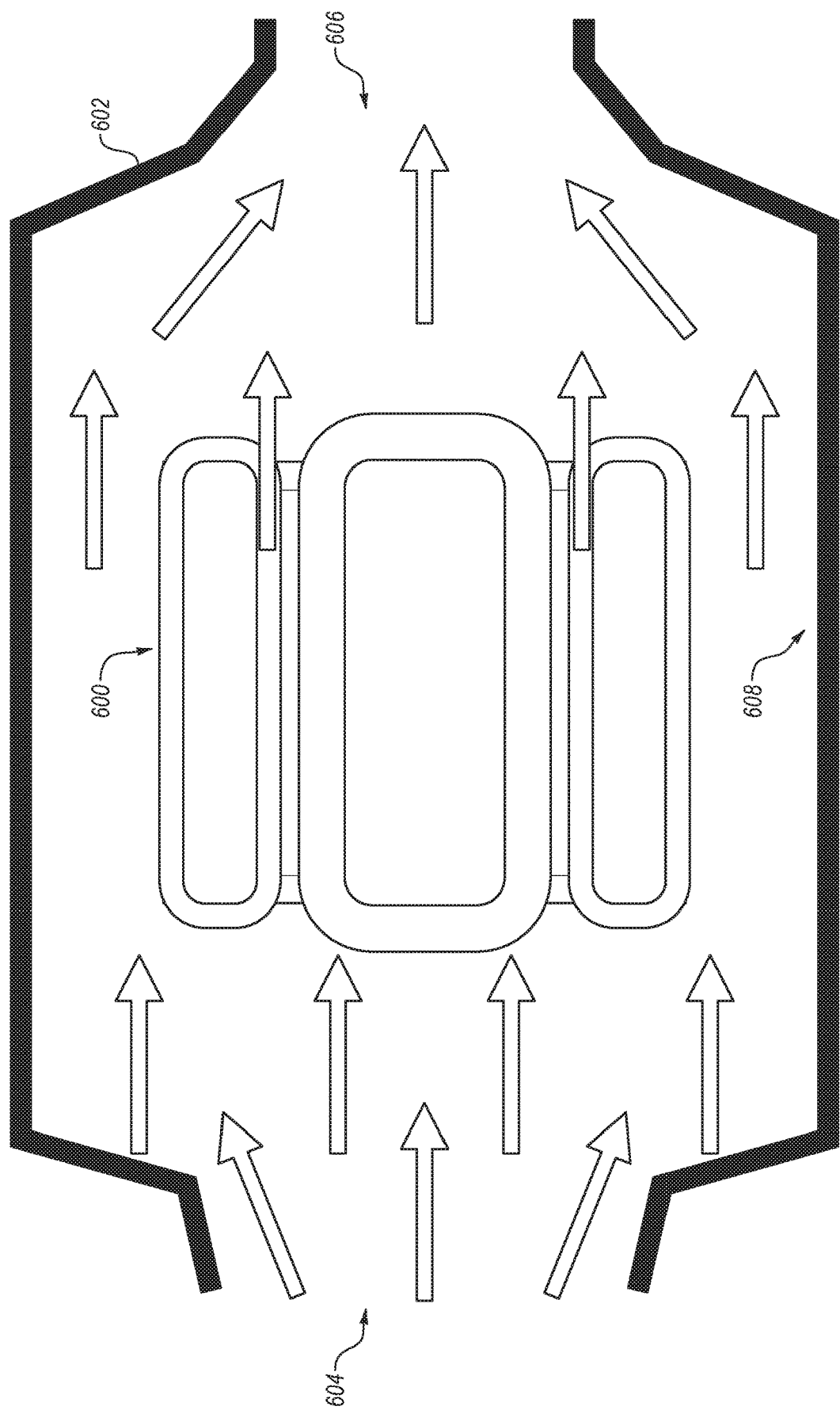
FIG. 8B is a bottom schematic view of the shroud of FIG. 8A.
Figure 8C:
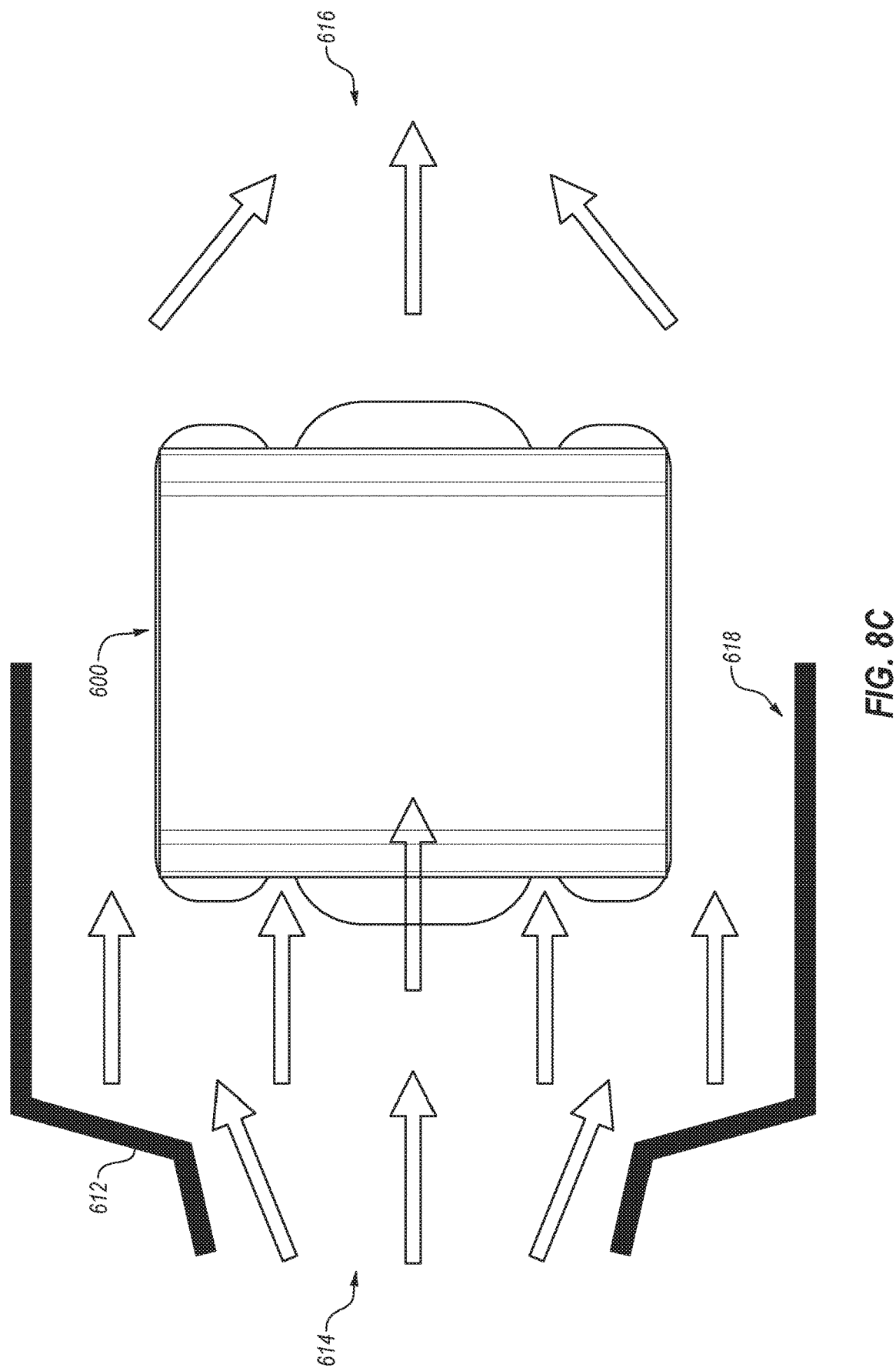
FIG. 8C is a top schematic view of an example shroud that directs flow around a lift electromagnet.
Figure 8D:
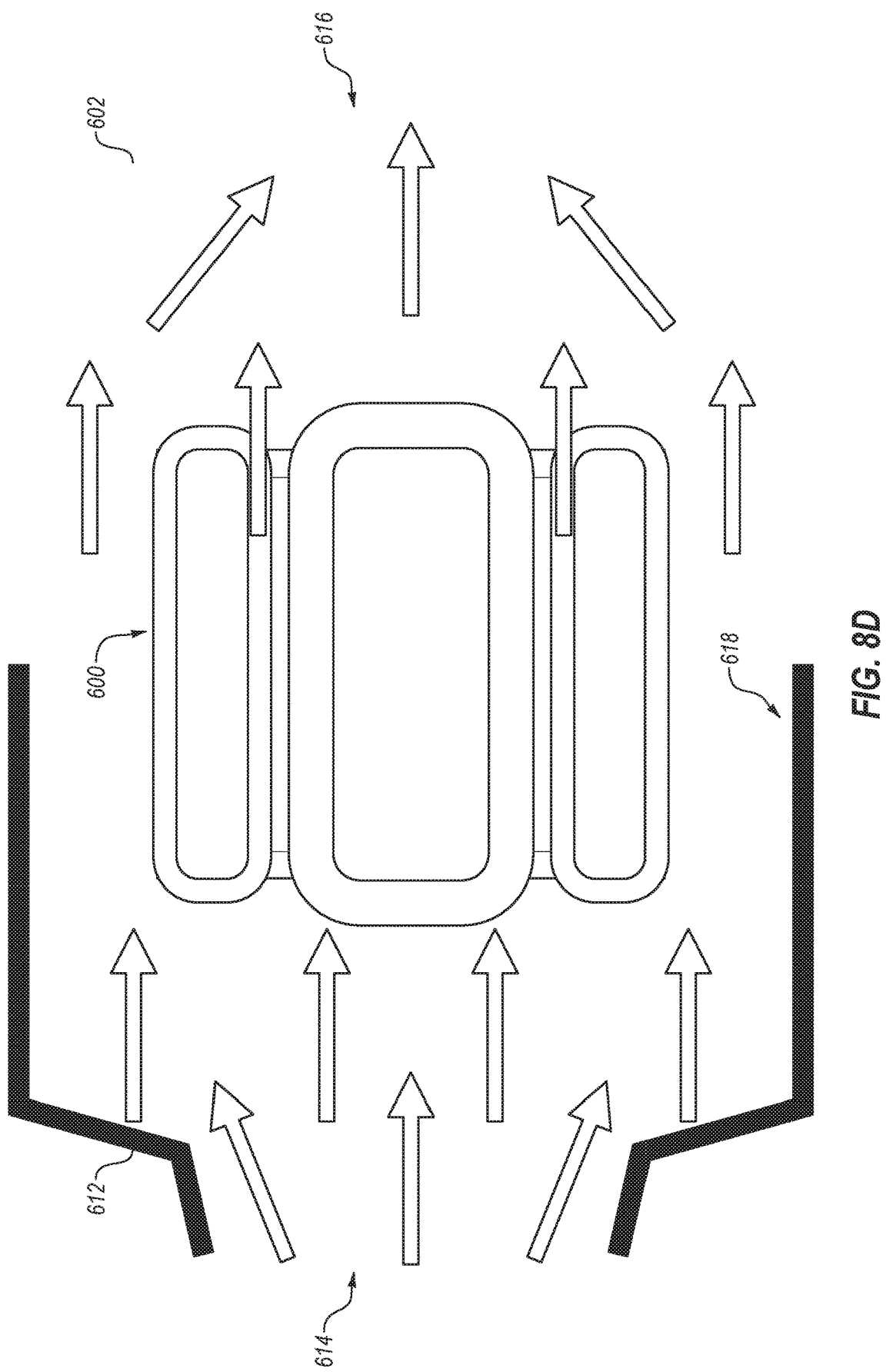
FIG. 8D is a bottom schematic view of the shroud of FIG. 8C.

In further configurations, a duct, shroud, or jet could be directed at a lift electromagnet. An example of such configurations is illustrated in FIGS. 8A-8D. FIG. 8A is a top schematic view and FIG. 8B is a bottom schematic view of an example shroud 602 (or duct or jet) that directs flow around a lift electromagnet 600. FIG. 8C is a top schematic view and FIG. 8D is a bottom schematic view of another example of a shroud 612 (or duct or jet) that directs flow around the lift electromagnet 600.

As illustrated in FIGS. 8A-8B, in some aspects the shroud 602 may include an inlet 604 and outlet 606, or any suitable number of inlets and outlets. The inlet 604 may permit coolant to enter a cavity 608 defined by the shroud and the outlet 606 may permit coolant to exit the cavity 608. The lift electromagnet 600 may be positioned at least partially or entirely in the cavity 608. The inlet 604 of the shroud may be fluidly coupled to an outlet of an aperture cooling duct, a duct run in parallel, or a separate duct.

As indicated by the arrows, the coolant may be forced around or through the lift electromagnet 600 at higher velocities in desired areas, for example, in between adjacent sets of windings. In one example, the shroud 602 may direct coolant proximate the windings and/or in between the poles of the lift electromagnet 600. Accordingly, in some embodiments at least some of the inlets may be aligned with the spaces in between the poles of the lift electromagnet 600. Although the shroud 602 is illustrated to be substantially surround the lift electromagnet 600, other configurations may be implemented.

For example, as illustrated in FIGS. 8C-8D, the shroud 612 partially surrounds the lift electromagnet 600. In such configurations, the shroud 612 defines a cavity 618 that receive and partially surrounds the lift electromagnet 600. In such configurations, the coolant may be forced around or through the lift electromagnet 600 at higher velocities in desired areas, as indicated by the arrows. The shroud 612 may include an inlet 614 and outlet 616, or any suitable number of inlets and outlets. The inlet 614 may permit coolant to enter a cavity 618 defined by the shroud 612 and the outlet 606 may permit coolant to exit the cavity 618.

As mentioned, the shrouds, ducts or jets may include any suitable number of inlets and/or outlets. In some configurations, a shroud may include at least two inlets, or may include four inlets, or any suitable number of inlets. The size of the inlets of the shroud may be selected to direct coolant in desired volumes or desired velocity around or through the lift electromagnet. For example, the inlets directing coolant in the spaces between the poles may be larger in size (e.g., diameter or at least one dimension) than the inlets directing coolant around the sides of the lift electromagnet. In such configurations, the different inlets will direct coolant at different volumes and velocities.

In some circumstances, the duct, shroud, or jet may be molded or 3D printed. In some aspects, the duct, shroud, or jet may include or may be formed of material that is resistant to degradation, contamination or damage from the coolant fluid. For example, the duct, shroud, or jet may be formed of a polymer.

In some embodiments, the duct, shroud, or jet could be included with the other heat dissipating structures described herein. For example, the duct, shroud, or jet could be included with fins, openings, or a thermal interface. In some aspects, the duct, shroud, or jet may align with the heat dissipating structures such as the fins or the openings. The duct, shroud, or jet may be configured to ensure that the forced flow cools the lift electromagnet with minimal leakage to the ambient volume of fluid in a housing surrounding the lift electromagnet without passing by the lift electromagnet.

As mentioned, in some embodiments the coolant that removes heat from areas of the lift electromagnet may be the same coolant that cools the other portions of the X-ray tube (e.g., the insert and/or stator assembly). In other embodiments, the lift electromagnet may use a separate coolant and/or cooling configurations than other portions of the X-ray tube. In such configurations, the coolant may be selected to improve cooling of the lift electromagnet, for example, by using a coolant with better thermal properties. For example, a coolant fluid may have a thermal conductivity of up to 0.2 W/(m·K). Although coolants with better thermal properties may be relatively more expensive, since the volume of coolant necessary to cool the lift electromagnet may be less than the volume of coolant required to cool the rest of the X-ray assembly, it may be cost effective to use a more expensive coolant to cool just the lift electromagnet.

In other embodiments, cooling fins may be included directly on the lift electromagnet (e.g., the core of the lift electromagnet) rather than on windings. Such configurations may be implemented if there is a relatively good thermal link between the core and the windings of the lift electromagnet. An example of such a configuration is illustrated in FIG. 9.

FIG. 9 is a schematic cross section of another example of a lift electromagnet 624. As illustrated, in some configurations, fins 624 may be positioned on the top of the lift electromagnet 624. In particular, the fins 624 may be positioned on a curved surface of a core 622 of the lift electromagnet 624. In some circumstances, the fins 624 may be machined into a surface of the electromagnet 624. In such configurations, the fins 624 may be include depths that correspond to the depth or radius of the curved surface.

In some configurations, the top of the lift electromagnet may be in contact with the housing of the X-ray tube for direct exposure to the exterior of the X-ray tube (e.g., when the lift electromagnet is at the same voltage potential as the X-ray tube housing). The X-ray tube may be surrounded by air or other fluid acting as a coolant, and fans or other cooling devices may be used to cool the housing. In such configurations, fins may be added to the exterior of the housing proximate the lift electromagnet to facilitate heat dissipation from the lift electromagnet to the air exterior of the housing of the X-ray tube. Such configurations may include free convection cooling or forced convection cooling via air flow as the gantry is rotating. In other configurations, the lift electromagnet may be positioned outside the housing of the X-ray tube, such configurations may permit the lift electromagnet to be cooled in other manners similar to those described herein.

Figure 10:
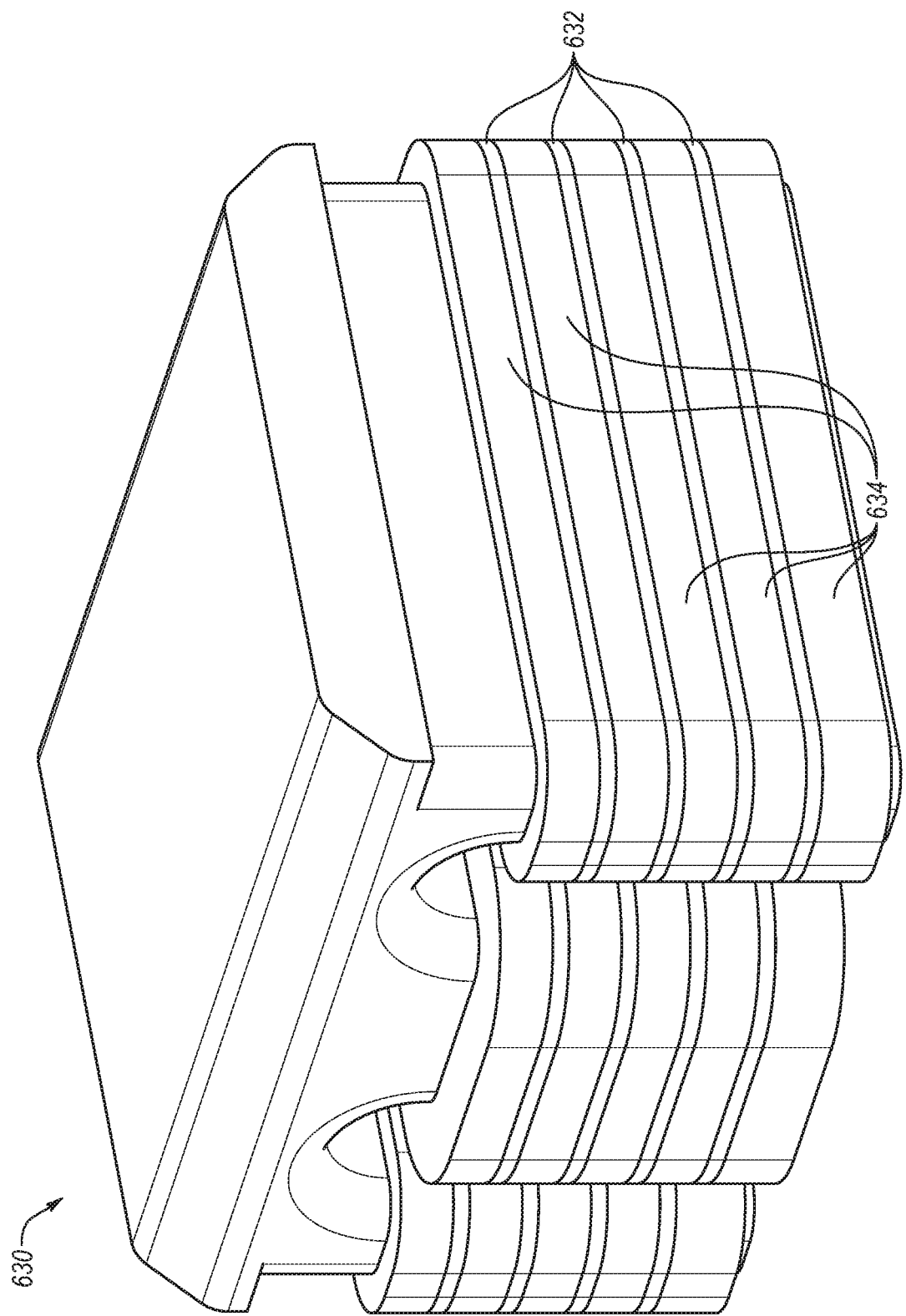
FIG. 10 is a perspective view of another example of a lift electromagnet.

In some embodiments, spacers may be positioned in between the turns of the windings to increase heat dissipation from the windings. An example of such a configuration is illustrated in FIG. 10. FIG. 10 is a perspective view of another example of a lift electromagnet 630. As illustrated, spacers 632 may be positioned in between the turns of the windings 634. Such configurations may increase heat dissipation from the windings 634. The spacers 632 may be formed of a material with relatively high heat conductivity. For example, the spacers 632 may include copper, gold, silver, diamond, boron nitride, aluminum, highly ordered pyrolytic graphite (HOPG) or other suitable materials. The spacers 632 may be a solid material or may be hollow on the inside. Configurations that include the spacers 632 may permit coolant fluid to flow in between adjacent turns of the windings, thereby facilitating cooling. Additionally or alternatively, the spacers 632 may include a void or multiple voids or openings to allow cooling fluid to penetrate the spacers 632 to facilitate cooling.

In one example, a lift assembly (220) may exert a force on a rotatable anode (242) of an X-ray tube. The lift assembly (220) may include a lift shaft (226) and a lift electromagnet (300, 400, 500, 600, 630). The lift shaft (226) may be coupled to the anode (242) and may be configured to rotate around an axis of rotation of the anode (242). The lift electromagnet (300, 400, 500, 600, 630) may be configured to apply a magnetic force to the lift shaft (226) in a radial direction. The lift electromagnet (300, 400, 500, 600, 630) may include a first pole and a second pole oriented towards the lift shaft (226). Windings (224) may be positioned around the first pole. The lift assembly (220) may include a heat dissipating structure.

The heat dissipating structure may include a duct, shroud, or jet (602, 612) configured to direct coolant around the lift electromagnet (300, 400, 500, 600, 630). The heat dissipating structure may include a shroud (602, 612) that at least partially surrounds the lift electromagnet (300, 400, 500, 600, 630) to force coolant around the lift electromagnet (300, 400, 500, 600, 630).

The heat dissipating structure may include one or more fins (416, 418) coupled to the windings (224), extending out of the windings (224), or embedded in the windings (224). The fins (416, 418) may be oriented parallel or perpendicular to the lift shaft (226). A largest dimension of the heat dissipating structure may be substantially parallel or perpendicular to the lift shaft (226).

The heat dissipating structure may be a thermal interface material (316) positioned on an external surface of the lift electromagnet (300, 400, 500, 600, 630), the windings (224), or between the lift electromagnet (300, 400, 500, 600, 630) and the windings (224). The thermal interface material (316) may have a higher thermal conductivity than a thermal conductivity of a coolant at least partially surrounding the lift electromagnet (300, 400, 500, 600, 630). The thermal interface material (316) may at least partially conforms to the windings (224). The thermal interface material (316) may include a thermal grease, epoxy, filler, or potting material.

The heat dissipating structure may include one or more openings (516, 518) extending through the lift electromagnet (300, 400, 500, 600, 630) in a direction of fluid flow. The openings (516, 518) may extend to a space between the first pole and the second pole. The heat dissipating structure may include one or more channels (520) positioned on the first pole and one or more openings (518) extending through the lift electromagnet (300, 400, 500, 600, 630) to the channels (520). A coolant may be positioned at least partially around the lift electromagnet (300, 400, 500, 600, 630).

In another example embodiment, a method may include rotating an anode assembly (240) of an X-ray source, applying a magnetic force by a lift electromagnet (300, 400, 500, 600, 630) to a lift shaft (226) coupled to the anode assembly (240), and cooling the lift electromagnet (300, 400, 500, 600, 630) using a heat dissipating structure. Cooling the lift electromagnet (300, 400, 500, 600, 630) may include directing a coolant at least partially around the lift electromagnet (300, 400, 500, 600, 630). Cooling the lift electromagnet (300, 400, 500, 600, 630) may include forcing a coolant at least partially around the lift electromagnet (300, 400, 500, 600, 630) using a duct, shroud, or jet that directs coolant around the lift electromagnet (300, 400, 500, 600, 630). Cooling the lift electromagnet (300, 400, 500, 600, 630) may include directing coolant through fins coupled to the lift electromagnet (300, 400, 500, 600, 630) or through openings or channels defined in the lift electromagnet (300, 400, 500, 600, 630).

In another example embodiment, a lift assembly (220) may be configured to exert a force on a rotatable anode (242) of an X-ray source. The lift assembly (220) may include a lift shaft means coupled to the anode (242) for rotating around an axis of rotation of the anode (242), a lift electromagnet (300, 400, 500, 600, 630) means for applying a magnetic force to the lift shaft in a radial direction, and heat dissipating means for cooling the lift electromagnet (300, 400, 500, 600, 630).

The terms and words used in this description and claims are not limited to the bibliographical meanings, but, are merely used to enable a clear and consistent understanding of the disclosure. It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those skilled in the art, may occur in amounts that do not preclude the effect the characteristic was intended to provide.

Aspects of the present disclosure may be embodied in other forms without departing from its spirit or essential characteristics. The described aspects are to be considered in all respects illustrative and not restrictive. The claimed subject matter is indicated by the appended claims rather than by the foregoing description. All changes which come within the meaning and range of equivalency of the claims are to be embraced within their scope.

What is claimed is:

1. A lift assembly configured to exert a force on a rotatable anode of an X-ray tube, the lift assembly comprising:
   a lift shaft coupled to the anode and configured to rotate around an axis of rotation of the anode;
   a lift electromagnet configured to apply a magnetic force to the lift shaft in a substantially radial direction, the lift electromagnet comprising at least a first pole and a second pole oriented towards the lift shaft;
   windings positioned around at least the first pole; and
   a heat dissipating structure.

2. The lift assembly of claim 1, wherein the heat dissipating structure comprises a duct, shroud, or jet configured to direct coolant around the lift electromagnet.

3. The lift assembly of claim 1, wherein the heat dissipating structure comprises a shroud that at least partially surrounds the lift electromagnet to force coolant around the lift electromagnet.

4. The lift assembly of claim 1, wherein the heat dissipating structure comprises one or more fins coupled to the windings, extending out of the windings, or embedded in the windings.

5. The lift assembly of claim 4, wherein the fins are oriented perpendicular to the lift shaft.

6. The lift assembly of claim 4, wherein the fins are oriented parallel to the lift shaft.

7. The lift assembly of claim 1, wherein a largest dimension of the heat dissipating structure is substantially parallel or perpendicular to the lift shaft.

8. The lift assembly of claim 1, wherein the heat dissipating structure is a thermal interface material positioned on an external surface of the lift electromagnet, the windings, or between the lift electromagnet and the windings.

9. The lift assembly of claim 8, wherein the thermal interface material has a higher thermal conductivity than a thermal conductivity of a coolant at least partially surrounding the lift electromagnet.

10. The lift assembly of claim 8, wherein the thermal interface material at least partially conforms to the windings or the thermal interface material comprises a thermal grease, epoxy, filler, or potting material.

11. The lift assembly of claim 1, wherein the heat dissipating structure comprises one or more openings extending through the lift electromagnet in a direction of fluid flow.

12. The lift assembly of claim 11, wherein the openings extend to a space between the first pole and the second pole.

13. The lift assembly of claim 1, further comprising one or more channels positioned on the first pole and one or more openings extending through the lift electromagnet to the channels.

14. The lift assembly of claim 1, further comprising a coolant positioned at least partially around the lift electromagnet.

15. The lift assembly of claim 1, wherein the windings comprise outer windings and inner windings, wherein the outer windings have a higher resistance than the inner windings.

16. A method comprising:
   rotating an anode assembly of an X-ray source;
   applying a magnetic force by a lift electromagnet to a lift shaft coupled to the anode assembly;
   cooling the lift electromagnet using a heat dissipating structure.

17. The method of claim 16, wherein the cooling of the lift electromagnet comprises directing a coolant at least partially around the lift electromagnet.

18. The method of claim 16, wherein the cooling of the lift electromagnet comprises forcing a coolant at least partially around the lift electromagnet using a duct, shroud, or jet that directs coolant around the lift electromagnet.

19. The method of claim 16, wherein the cooling of the lift electromagnet comprises directing coolant through fins coupled to the lift electromagnet or through openings or channels defined in the lift electromagnet.

20. A lift assembly configured to exert a force on a rotatable anode of an X-ray source, the lift assembly comprising:
   a lift shaft means coupled to the anode for rotating around an axis of rotation of the anode;
   a lift electromagnet means for applying a magnetic force to the lift shaft in a radial direction; and
   heat dissipating means for cooling the lift electromagnet.

* * * * *